(12) United States Patent
Medarova et al.

(10) Patent No.: US 10,463,627 B2
(45) Date of Patent: *Nov. 5, 2019

(54) THERAPEUTIC NANOPARTICLES AND METHODS OF USE THEREOF

(71) Applicant: The General Hospital Corporation, Boston, MA (US)

(72) Inventors: Zdravka Medarova, Methuen, MA (US); Mehmet V. Yigit, Delmar, NY (US); Anna Moore, Stoneham, MA (US)

(73) Assignee: The General Hospital Corporation, Boston, MA (US)

( * ) Notice: Subject to any disclaimer, the term of this patent is extended or adjusted under 35 U.S.C. 154(b) by 137 days.

This patent is subject to a terminal disclaimer.

(21) Appl. No.: 15/699,796

(22) Filed: Sep. 8, 2017

(65) Prior Publication Data

US 2018/0055781 A1    Mar. 1, 2018

Related U.S. Application Data

(63) Continuation of application No. 14/233,215, filed as application No. PCT/US2012/047366 on Jul. 19, 2012, now Pat. No. 9,763,891.

(60) Provisional application No. 61/510,563, filed on Jul. 22, 2011.

(51) Int. Cl.

| | |
|---|---|
| *A61K 9/51* | (2006.01) |
| *A61K 39/395* | (2006.01) |
| *A61K 45/06* | (2006.01) |
| *A61K 47/62* | (2017.01) |
| *A61K 47/69* | (2017.01) |
| *A61K 49/18* | (2006.01) |
| *A61K 9/50* | (2006.01) |
| *A61K 9/00* | (2006.01) |
| *A61K 31/7115* | (2006.01) |
| *C12N 15/11* | (2006.01) |
| *C12N 15/113* | (2010.01) |
| *A61N 5/10* | (2006.01) |
| *A61K 31/713* | (2006.01) |
| *B82Y 5/00* | (2011.01) |
| *A61K 39/00* | (2006.01) |

(52) U.S. Cl.
CPC .............. *A61K 9/51* (2013.01); *A61K 9/0009* (2013.01); *A61K 9/5036* (2013.01); *A61K 9/5063* (2013.01); *A61K 9/5115* (2013.01); *A61K 31/713* (2013.01); *A61K 31/7115* (2013.01); *A61K 39/39558* (2013.01); *A61K 45/06* (2013.01); *A61K 47/62* (2017.08); *A61K 47/6923* (2017.08); *A61K 49/1824* (2013.01); *A61N 5/10* (2013.01); *C12N 15/111* (2013.01); *C12N 15/113* (2013.01); *A61K 2039/505* (2013.01); *B82Y 5/00* (2013.01); *C12N 2310/11* (2013.01); *C12N 2310/113* (2013.01); *C12N 2310/14* (2013.01); *C12N 2310/3231* (2013.01); *C12N 2310/351* (2013.01); *C12N 2320/31* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 8,404,659 B2 | 3/2013 | Kauppinen et al. | |
| 9,629,812 B2* | 4/2017 | Medarova | ............... A61K 9/51 |
| 9,763,891 B2* | 9/2017 | Medarova | ............... A61K 9/51 |
| 2008/0056998 A1 | 3/2008 | Wellington et al. | |
| 2010/0119444 A1 | 5/2010 | Wu et al. | |

FOREIGN PATENT DOCUMENTS

| | | |
|---|---|---|
| RU | 2344831 | 1/2009 |
| WO | WO 2011/003109 | 1/2011 |

OTHER PUBLICATIONS

Chen et al., "Nanoparticles Modified with Tumor-targeting scFv Deliver siRNA and miRNA for Cancer Therapy," Molecular Therapy, Sep. 2010, 18(9):1650-1656.
Elias et al., "Imaging circulating cells and lymphoid tissues with iron oxide nanoparticles," Nanotechnology for Hematology, Jan. 2009, 720-726.
Final Office Action in U.S. Appl. No. 14/233,215, dated Feb. 23, 2016, 11 pages.
Gebeshuber, et al. (2009) "miR-29a suppresses tristetraprolin, which is a regulator of epithelial polarity and metastasis", EMBO Reports, Apr. 2009, 10(4): 400-405.
International Preliminary Report on Patentability in International Application No. PCT/US2012/047366, dated Oct. 8, 2012, 6 pages.
International Search Report and Written Opinion dated Dec. 13, 2012 in international application No. PCT/US2012/047366, 7 pgs.
Kumar et al., "Image-Guided Breast Tumor Therapy Using a Small Interfering RNA Nanodrug," Cancer Research, Oct. 2010, 70:7553-7561.
Ma et al., "Therapeutic silencing of miR-10b inhibits metastasis in a mouse mammary tumor model," Nature Biotechnology, Mar. 2010, 28: 341-347.

(Continued)

*Primary Examiner* — Robert M Kelly
(74) *Attorney, Agent, or Firm* — Fish & Richardson P.C.

(57) ABSTRACT

Provided herein are therapeutic nanoparticles having a diameter of between 10 nm to 30 nm, and containing a polymer coating, and a nucleic acid containing a sequence complementary to a sequence within a micro-RNA identified as having a role in cancer cell metastasis or anti-apoptotic activity in a cancer cell (e.g., miR-10b) or a sequence within an mRNA encoding a pro-apoptotic protein that is covalently linked to the nanoparticle. Also provided are pharmaceutical compositions containing these therapeutic nanoparticles. Also provided herein are methods of decreasing cancer cell invasion or metastasis in a subject having a cancer and methods of treating a metastatic cancer in a lymph node in a subject that require the administration of these therapeutic nanoparticles to a subject.

28 Claims, 11 Drawing Sheets

Specification includes a Sequence Listing.

(56) References Cited

OTHER PUBLICATIONS

Ma et al., "Tumour invasion and metastasis initiated by microRNA-10b in breast cancer," Nature, Oct. 2007, 449:682-688.

Ma et al., "MicroRNA-616 induces androgen-independent growth of prostate cancer cells by suppressing expression of tissue factor pathway inhibitor TFPI-2," Cancer Research, Jan. 2011, 71(2):583-92.

Ma, "Role of miR-10b in breast cancer metastasis", Breast Cancer Research, Oct. 2010, 12(5):210.

Medarova et al., "In vivo imaging of siRNA delivery and silencing in tumors," Nature Medicine, Mar. 2007, 13(3):372-377.

Moriarty et al., "miR-10b Targets Tiam1: Implications for Rac Activation and Carcinoma Migration", The Journal of Biological Chemistry, Jul. 2010, 285: 20541-46.

Non-final Office Action in U.S. Appl. No. 14/233,215, dated Jul. 13, 2015, 10 pages.

Non-final Office Action in U.S. Appl. No. 14/233,215, dated Aug. 11, 2016, 12 pages.

Non-final Office Action in U.S. Appl. No. 14/233,215, dated Jan. 20, 2017, 18 pages.

Peng et al., "Targeted magnetic iron oxide nanoparticles for tumor imaging and therapy," International Journal of Nanomedicine, Sep. 2008, 3(3):311-321.

Rasmussen and Roberts, "Functional studies of microRNA based knockdown using Locked Nucleic Acid probes", Nature Methods, Apr. 2007, 4: iii-iv.

Yang, et al., "Inhibition of proliferative and invasive capacities of breast cancer cells by arginine-glycine-aspartic acid peptide in vitro", Oncology Reports, Jan. 2006, 15(1): 113-17.

Yigit, et al., "Context-dependent differences in miR-10b breast oncogenesis can be targeted for the prevention and arrest of lymph node metastasis", Oncogene, Mar. 2013, 32(12): 1530-38.

Author Unknown, 2016, http://www.cancer.net/cancer-types/breast-cancer/overview, Approved by the Cancer.Net Editorial Board, Alexandria, VA, no volume, no issue, printed as 4 pages.

* cited by examiner

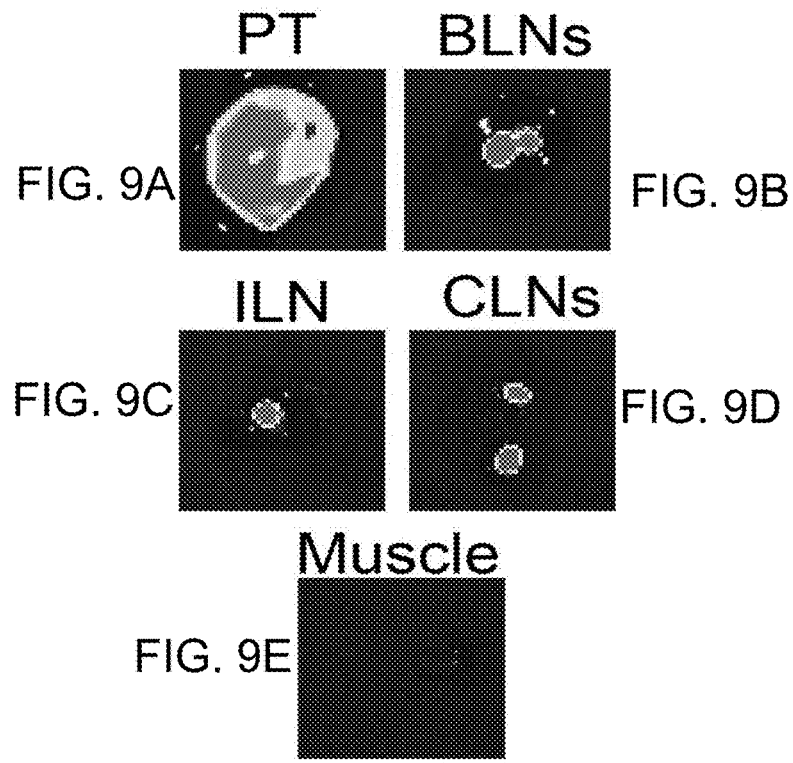
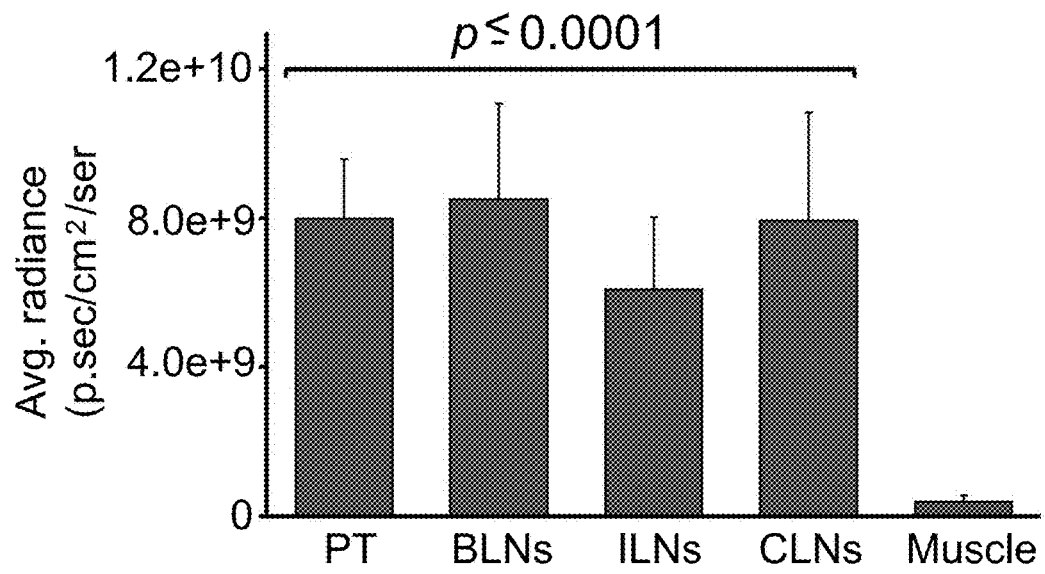
FIG. 10   MN-scr-miR

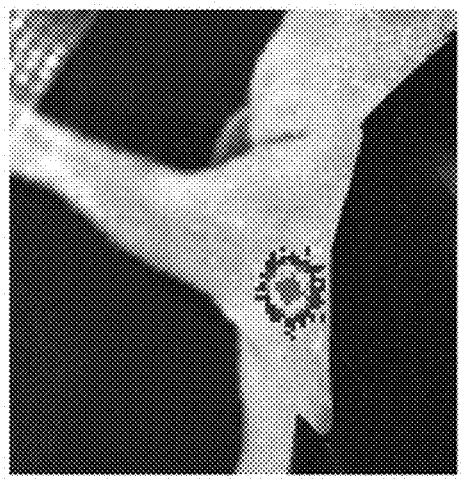 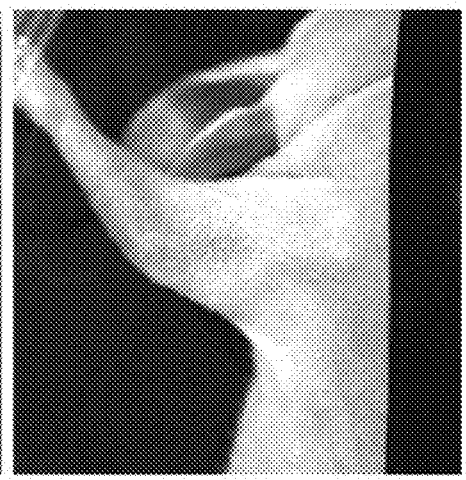
MN-scr-miR    MN-anti-miR10b
FIG. 11A    FIG. 11B
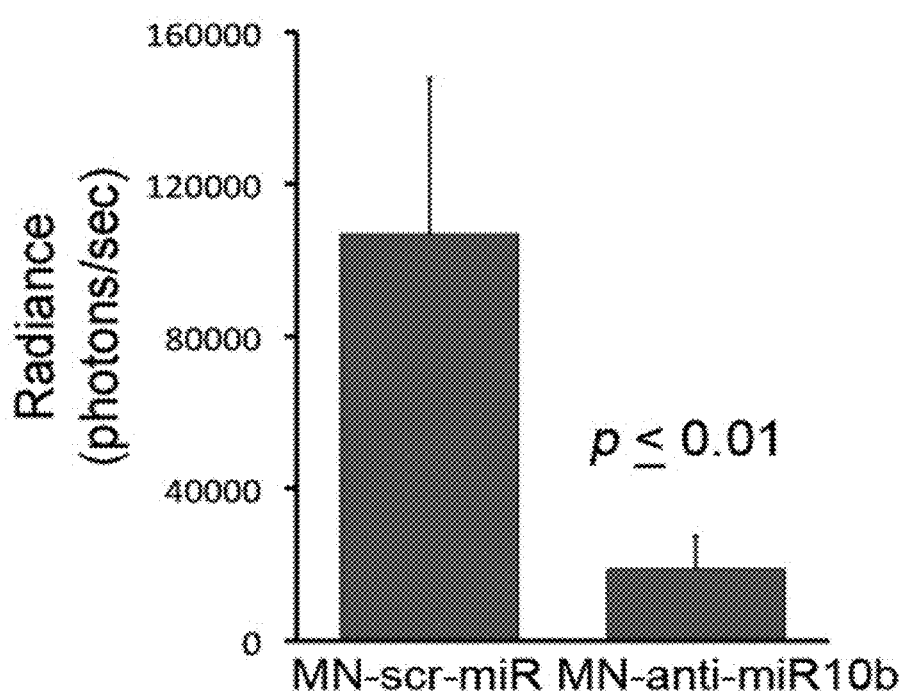
FIG. 12

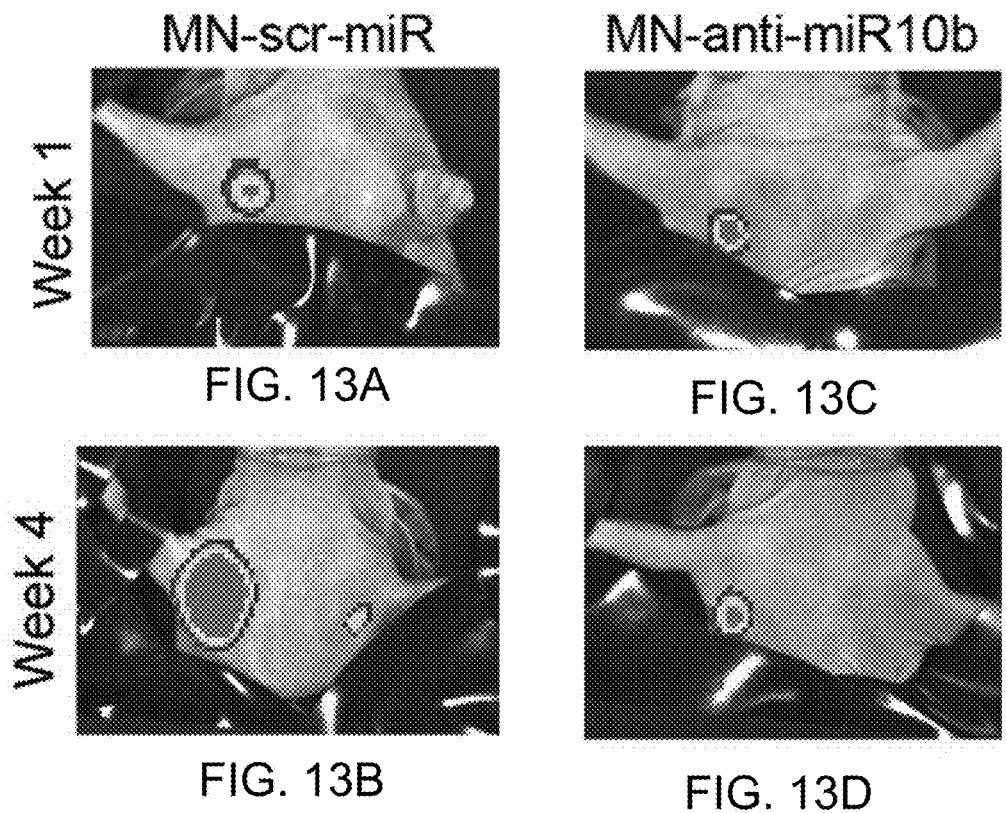
FIG. 13A  FIG. 13C
FIG. 13B  FIG. 13D
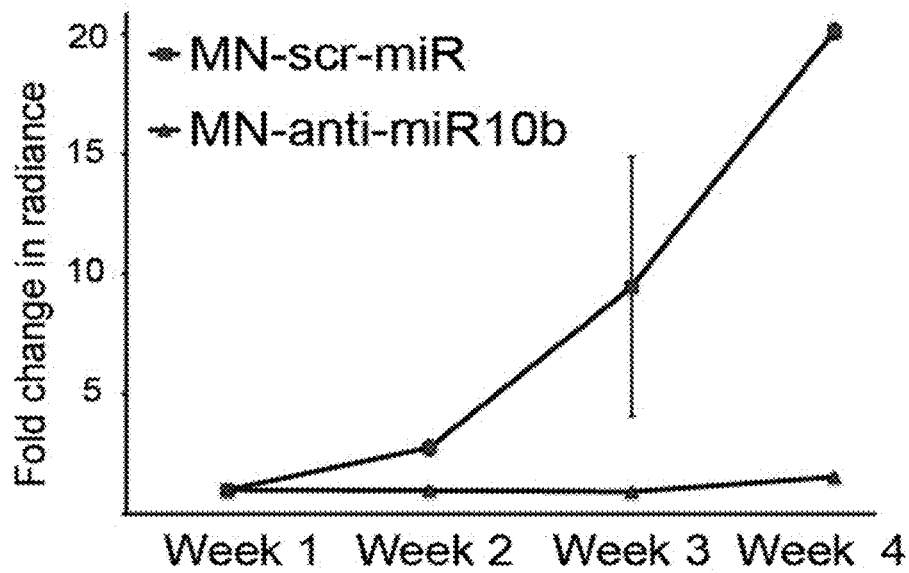
FIG. 14

THERAPEUTIC NANOPARTICLES AND METHODS OF USE THEREOF

CROSS-REFERENCE TO RELATED APPLICATION

This application is a continuation of U.S. Ser. No. 14/233,215, filed Apr. 11, 2014, now U.S. Pat. No. 9,763,891, which is a National Stage application under 35 U.S.C. § 371 that claims the benefit of PCT/US2012/047366, filed Jul. 19, 2012, which claims the benefit of U.S. Provisional Application No. 61/510,563 filed Jul. 22, 2011, the disclosures of which are hereby incorporated by reference in their entirety.

TECHNICAL FIELD

This invention relates to therapeutic nanoparticples containing a polymer coating and a covalently-linked inhibitory nucleic acid, compositions containing these therapeutic nanoparticles, and methods of using these therapeutic nanoparticles.

BACKGROUND

Breast cancer is the second leading cause of cancer-related deaths in women of the Western world. In the U.S.A. alone, over 180,000 new cases of breast cancer are diagnosed each year. Of these patients, approximately 25% will die despite aggressive diagnostic and therapeutic intervention. Despite the considerable and recent improvement in breast cancer diagnostics and therapy, the morbidity and mortality associated with this disease remain alarming.

The best chance for survival of breast cancer is to detect the cancer before it has had a chance to metastasize. Unfortunately, breast cancer can reappear and metastasis can occur even if the cancer was confined to the breast at the time of detection. Once metastatic breast cancer has been diagnosed, it can be treated. However, in most cases, none of the treatments lead to long-term survival.

One of the pathways for breast cancer systemic metastasis involves the passage of cancer cells through the lymphatic system. There is convincing experimental support for a metastatic breast cancer model that has an early state, in which the breast cancer cells are confined to the breast and the regional lymph nodes, and have not yet metastasized to distant sites. Additional recent preclinical and clinical immunohistochemical, physiologic, and pathophysiologic metastatic breast cancer studies support a model of breast cancer metastasis where the breast cancer cells first invade peritumoral lymphatics, then spread to locoregional lymph nodes, prior to hematogenous metastasis in a subject.

SUMMARY

This disclosure describes therapeutic nanoparticles that have a diameter of between 2 nm to 200 nm (e.g., between 10 nm and 200 nm, between 2 nm and 30 nm, between 5 nm and 30 nm, between 10 nm and 30 nm, between 15 to 25 nm, or between 20 to 25 nm), and contain a polymer coating and a nucleic acid containing a sequence that is complementary to a contiguous sequence present within a microRNA (miRNA) identified as having a role in cancer cell metastasis or invasion, or anti-apoptotic activity in a cancer cell (e.g., miR-10b), or a contiguous sequence present within an mRNA encoding a pro-apoptotic protein that is covalently linked to the nanoparticle. In some implementations, the therapeutic nanoparticles are magnetic (e.g., contain a magnetic core material). Also provided are pharmaceutical compositions containing these therapeutic nanoparticles, and methods of decreasing cancer cell invasion or metastasis in a subject and methods of treating metastatic cancer in a lymph node in a subject that include the administration of these therapeutic nanoparticles.

The therapeutic nanoparticles can have a diameter of between 10 nm to 30 nm (e.g., between 15 to 25 nm or between 20 to 25 nm), and can include a polymer coating (e.g., a polymer coating containing dextran) and a nucleic acid containing at least 10 (e.g., between 10-15 nucleotides or between 15 to 20 nucleotides) contiguous nucleotides within the sequence of GTGTAACACGTCTATACGCCCA (SEQ ID NO: 17), ATGGGACATCTTGGCTTAAACAC (SEQ ID NO: 1) or TGTCTAAGCTAAGAT CCCCTTA (SEQ ID NO: 2) that is covalently linked to the nanoparticle. In some implementations, the nucleic acid contains at least one (e.g., at least two, three, or four) modified nucleotide(s) (e.g., a nucleotide containing a base modification or a ribose or deoxyribose modification) or one or more modifications in the phosphate (phosphodiester) backbone. In some implementations, the modified nucleotide is a locked nucleotide. In some embodiments, the nucleic acid is single-stranded or double stranded. In some embodiments, the nucleic acid is a small interfering RNA (siRNA) molecule. In some implementations, the nucleic acid is covalently-linked to the nanoparticle through a chemical moiety containing a disulfide bond. In some embodiments, the nucleic acid is covalently linked to the nanoparticle through a chemical moiety containing a thioether bond.

In some implementations, the therapeutic nanoparticle further contains a covalently-linked fluorophore (e.g., a fluorophore that absorbs near-infrared light). In some embodiments, the fluorophore is covalently linked to the nanoparticle through a chemical moiety that contains a secondary amine.

In some embodiments, the therapeutic nanoparticle further contains a covalently-linked targeting peptide. In some embodiments, the targeting peptide contains an RGD peptide, an EPPT peptide, NYLHNHPYGTVG (SEQ ID NO: 11), SNPFSKPYGLTV (SEQ ID NO: 12), GLHESTFTQRRL (SEQ ID NO: 13), YPHYSLPGSSTL (SEQ ID NO: 14), SSLEPWHRTTSR (SEQ ID NO: 15), LPLALPRHNASV (SEQ ID NO: 16), or βAla-(Arg)$_7$-Cys (SEQ ID NO: 19). In some embodiments, the targeting peptide is covalently linked to the nanoparticle through a chemical moiety that contains a disulfide bond. In some embodiments, the therapeutic nanoparticle is magnetic.

Also provided are pharmaceutical compositions containing any of the magnetic particles described herein.

Also provided are methods for decreasing cancer cell invasion or metastasis in a subject having a cancer (e.g., breast cancer) that include administering a therapeutic nanoparticle (any of the therapeutic nanoparticles described herein) to a subject having a cancer, where the therapeutic nanoparticle is administered in an amount sufficient to decrease cancer cell invasion or metastasis in the subject. In some embodiments, the cancer cell metastasis is from a primary tumor to a lymph node in the subject or is from a lymph node to a secondary tissue in a subject. In some embodiments, the cancer cell is selected from the group of: a breast cancer cell, a colon cancer cell, a kidney cancer cell, a lung cancer cell, a skin cancer cell, an ovarian cancer cell, a pancreatic cancer cell, a prostate cancer cell, a rectal cancer cell, a stomach cancer cell, a thyroid cancer cell, and a uterine cancer cell. Some embodiments of these methods further include imaging a tissue of the subject to determine the location or number of cancer cells in the subject, or the location of the therapeutic nanoparticles (e.g., the location of therapeutic magnetic nanoparticles or therapeutic nanoparticles containing a covalently-linked fluorophore) in the subject.

In another aspect, the disclosure describes methods of treating a metastatic cancer in a lymph node in a subject. These methods include administering a therapeutic nanoparticle (any of the therapeutic nanoparticles described herein) to a lymph node of a subject having a metastatic cancer, where the therapeutic nanoparticle is administered in an amount sufficient to treat a metastastic cancer in a lymph node in the subject. In some embodiments, the metastatic cancer results from a primary breast cancer. In some embodiments, the administering results in a decrease (e.g., a significant, detectable, or observable decrease) or stabilization of metastatic tumor size or a decrease (e.g., a significant, detectable, or observable decrease) in the rate of metastatic tumor growth in a lymph node in the subject.

In any of the methods described herein, the therapeutic nanoparticles can be administered in multiple doses to the subject. In some embodiments of the methods described herein, the therapeutic nanoparticles are administered to the subject at least once a week. In some embodiments of the methods described herein, the therapeutic nanoparticles are administered to the subject by intravenous, subcutaneous, intraarterial, intramuscular, or intraperitoneal administration. In some embodiments of the methods described herein, the subject is further administered a chemotherapeutic agent.

The term "magnetic" is used to describe a composition that is responsive to a magnetic field. Non-limiting examples of magnetic compositions (e.g., any of the therapeutic nanoparticles described herein) can contain a material that is paramagnetic, superparamagnetic, ferromagnetic, or diamagnetic. Non-limiting examples of magnetic compositions contain a metal oxide selected from the group of: magnetite; ferrites (e.g., ferrites of manganese, cobalt, and nickel); Fe(II) oxides; and hematite, and metal alloys thereof. Additional magnetic materials are described herein and are known in the art.

The term "diamagnetic" is used to describe a composition that has a relative magnetic permeability that is less than or equal to 1 and that is repelled by a magnetic field.

The term "paramagnetic" is used to describe a composition that develops a magnetic moment only in the presence of an externally-applied magnetic field.

The term "ferromagnetic" or "ferromagnetic" is used to describe a composition that is strongly susceptible to magnetic fields and is capable of retaining magnetic properties (a magnetic moment) after an externally-applied magnetic field has been removed.

By the term "nanoparticle" is meant an object that has a diameter between about 2 nm to about 200 nm (e.g., between 10 nm and 200 nm, between 2 nm and 100 nm, between 2 nm and 40 nm, between 2 nm and 30 nm, between 2 nm and 20 nm, between 2 nm and 15 nm, between 100 nm and 200 nm, and between 150 nm and 200 nm). Non-limiting examples of nanoparticles include the therapeutic nanoparticles described herein.

By the term "magnetic nanoparticle" is meant a nanoparticle (e.g., any of the therapeutic nanoparticles described herein) that is magnetic (as defined herein). Non-limiting examples of magnetic nanoparticles are described herein. Additional magnetic nanoparticles are known in the art.

By the term "polymer coating" is meant at least one molecular layer (e.g., homogenous or non-homogenous) of at least one polymer (e.g., dextran) applied to a surface of a three-dimensional object (e.g., a three-dimensional object containing a magnetic material, such as a metal oxide). Non-limiting examples of polymers that can be used to generate a polymer coating are described herein. Additional examples of polymers that can be used to generate a polymer coating are known in the art. Methods for applying a polymer coating to an object (e.g., a three-dimensional object containing a magnetic material) are described herein and are also known in the art.

By the term "nucleic acid" is meant any single- or double-stranded polynucleotide (e.g., DNA or RNA, cDNA, semi-synthetic, or synthetic origin). The term nucleic acid includes oligonucleotides containing at least one modified nucleotide (e.g., containing a modification in the base and/or a modification in the sugar) and/or a modification in the phosphodiester bond linking two nucleotides. In some embodiments, the nucleic acid can contain at least one locked nucleotide (LNA). Non-limiting examples of nucleic acids are described herein. Additional examples of nucleic acids are known in the art.

By the term "modified nucleotide" is meant a DNA or RNA nucleotide that contains at least one modification in its base and/or at least one modification in its sugar (ribose or deoxyribose). A modified nucleotide can also contain modification in an atom that forms a phosphodiester bond between two adjoining nucleotides in a nucleic acid sequence.

By the term "fluorophore" is meant a molecule that absorbs light at a first wavelength and emits light at a second wavelength, where the first wavelength is shorter (higher energy) than the second wavelength. In some embodiments, the first wavelength absorbed by the fluorophore can be in the near-infrared range. Non-limiting examples of fluorophores are described herein. Additional examples of fluorophores are known in the art.

By the term "near-infrared light" is meant light with a wavelength of between about 600 nm to about 3,000 nm.

By the term "targeting peptide" is meant a peptide that is bound by a molecule (e.g., protein, sugar, or lipid, or combination thereof) present in or on the plasma membrane of a target cell (e.g., a cancer cell). As described herein, a targeting peptide can be covalently linked to a secondary molecule or composition (e.g., any of the therapeutic nanoparticles described herein) to target the secondary molecule or composition to a target cell (e.g., a cancer cell). In some embodiments, a targeting peptide that is covalently linked to a secondary molecule or composition (e.g., any of the therapeutic nanoparticles described herein) results in the uptake of the secondary molecule or composition by the targeted cell (e.g., cellular uptake by endocytosis or pinocytosis). Non-limiting examples of targeting peptides are described herein. Additional examples of targeting peptides are known in the art.

By the term "small interfering RNA" or "siRNA" is meant a double-stranded nucleic acid molecule that is capable of mediating RNA interference in a cell. The process of RNA interference is described in Ebalshir et al. (Nature 411:494-498, 2001). Each strand of a siRNA can be between 19 and 23 nucleotides in length. As used herein, siRNA molecules need not be limited to those molecules containing only native or endogenous RNA nucleotides, but can further encompass chemically-modified nucleotides. Non-limiting examples of siRNA are described herein. Additional examples of siRNA are known in the art.

By the phrase "cancer cell invasion" is meant the migration of a cancer cell into a non-cancerous tissue in a subject. Non-limiting examples of cancer cell invasion include: the migration of a cancer cell into a lymph node, the lymph, the vasculature (e.g., adventita, media, or intima of a blood vessel), or an epithelial or endothelial tissue. Exemplary methods for detecting and determining cancer cell invasion are described herein. Additional methods for detecting and determining cancer cell invasion are known in the art.

By the term "metastasis" is meant the migration of a cancer cell present in a primary tumor to a secondary, non-adjacent tissue in a subject. Non-limiting examples of metastasis include: metastasis from a primary tumor to a lymph node (e.g., a regional lymph node), bone tissue, lung tissue, liver tissue, and/or brain tissue. The term metastasis also includes the migration of a metastatic cancer cell found in a lymph node to a secondary tissue (e.g., bone tissue, liver tissue, or brain tissue). In some non-limiting embodiments, the cancer cell present in a primary tumor is a breast cancer cell, a colon cancer cell, a kidney cancer cell, a lung cancer cell, a skin cancer cell, an ovarian cancer cell, a pancreatic cancer cell, a prostate cancer cell, a rectal cancer cell, a stomach cancer cell, a thyroid cancer cell, or a uterine cancer cell. Additional aspects and examples of metastasis are known in the art or described herein.

By the term "primary tumor" is meant a tumor present at the anatomical site where tumor progression began and proceeded to yield a cancerous mass. In some embodiments, a physician may not be able to clearly identify the site of the primary tumor in a subject.

By the term "metastatic tumor" is meant a tumor in a subject that originated from a tumor cell that metastasized from a primary tumor in the subject. In some embodiments, a physician may not be able to clearly identify the site of the primary tumor in a subject.

By the term "lymph node" is meant a small spherical or oval-shaped organ of the immune system that contains a variety of cells including B-lymphocytes, T-lymphocytes, and macrophages, which is connected to the lymphatic system by lymph vessels. A variety of lymph nodes are present in a mammal including, but not limited to: axillary lymph nodes (e.g., lateral glands, anterior or pectoral glands, posterior or subscapular glands, central or intermediate glands, or medial or subclavicular glands), sentinel lymph nodes, sub-mandibular lymph nodes, anterior cervical lymph nodes, posterior cervical lymph nodes, supraclavicular lymph nodes, sub-mental lymph nodes, femoral lymph nodes, mesenteric lymph nodes, mediastinal lymph nodes, inguinal lymph nodes, sub segmental lymph nodes, segmental lymph nodes, lobar lymph nodes, interlobar lymph nodes, hilar lymph nodes, supratrochlear glands, deltoideopectoral glands, superficial inguinal lymph nodes, deep inguinal lymph nodes, brachial lymph nodes, and popliteal lymph nodes.

By the term "imaging" is meant the visualization of at least one tissue of a subject using a biophysical technique (e.g., electromagentic energy absorption and/or emission). Non-limiting embodiments of imaging include: magnetic resonance imaging (MM), X-ray computed tomography, and optical imaging.

By the phrase "stabilization of metastatic tumor size" is meant that a tumor has reached a stage in which there is only an insignificant or non-detectable change in the total or approximate volume of a metastatic tumor in a subject over time.

By the phrase "rate of metastatic tumor growth" is meant a change in the total or approximate volume of a metastatic tumor or a change in the total or approximate number of cells present in a metastatic tumor over time in a subject. The rate of metastatic tumor growth can be determined using the exemplary methods described herein. Additional methods for determining the rate of metastatic tumor growth are known in the art.

By the term "chemotherapeutic agent" is meant a molecule that can be used to reduce the rate of cancer cell growth or to induce or mediate the death (e.g., necrosis or apoptosis) of cancer cells in a subject (e.g., a human). In non-limiting examples, a chemotherapeutic agent can be a small molecule, a protein (e.g., an antibody, an antigen-binding fragment of an antibody, or a derivative or conjugate thereof), a nucleic acid, or any combination thereof. Non-limiting examples of chemotherapeutic agents include: cyclophosphamide, mechlorethamine, chlorabucil, melphalan, daunorubicin, doxorubicin, epirubicin, idarubicin, mitoxantrone, valrubicin, paclitaxel, docetaxel, etoposide, teniposide, tafluposide, azacitidine, axathioprine, capecitabine, cytarabine, doxifluridine, fluorouracil, gemcitabine, mercaptopurine, methotrexate, tioguanine, bleomycin, carboplatin, cisplatin, oxaliplatin, all-trans retinoic acid, vinblastine, vincristine, vindesine, vinorelbine, and bevacizumab (or an antigen-binding fragment thereof). Additional examples of chemotherapeutic agents are known in the art.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 9A-E are a set of five ex vivo images of a excised primary human breast cancer tumor (PT)(9A), brachial lymph nodes (BLNs)(9B), an inguinal lymph node (ILN) (9C), a cervical lymph node (CLN)(9D), and muscle (9E) showing the distribution of MN-RGD-anti-miR-10b (derived from a 23-nm MN precursor) after in vivo delivery into a MDA-MB-231-luc-D3H2LN mouse model.

FIG. 10 is a graph showing the average radiance of excised primary human breast cancer tumors (PT), brachial lymph nodes (BLNs), inguinal lymph nodes (ILNs), cervical lymph nodes (CLNs), and muscle following in vivo delivery of MN-RGD-anti-miR-10b. The data shown are the mean±standard deviation ($p \leq 0.0001$, n=6).

FIGS. 11A and 11B are two representative bioluminescence images of tumor-bearing MDA-MB-231-D3H2LN mice treated with MN-RGD-anti-miR-10b (11B) or a control MN-scr-miR (11A) for four weeks beginning prior to lymph node metastasis.

FIG. 12 is a graph of the bioluminescence of lymph node tissue in tumor-bearing MDA-MB-231-D3H2LN mice treated with MN-RGD-anti-miR-10b or a control MN-scr-miR for four weeks beginning prior to lymph node metastasis. The data shown are the mean±standard error ($p \leq 0.01$, n=3).

FIGS. 13A-D are a set of four representative bioluminescence images of tumor-bearing MDA-MB-231-D3H2LN mice treated with MN-RGD-anti-miR-10b for four weeks beginning subsequent to lymph node metastasis. The mice were either treated with MN-anti-miR10b (13C and 13D) or control MN-scr-miR (13A and 13D). Images taken at 1 week subsequent to lymph node metastasis (top panels) and 4 weeks subsequent to lymph node metastasis (bottom panels) are shown.

FIG. 14 is a graph showing the fold change in the radiance of brachial lymph nodes from tumor-bearing MDA-MB-231-D3H2LN mice treated with the MN-anti-miR10b compared to the radiance of brachial lymph nodes from tumor-bearing mice treated with MN-scr-miR at different time points subsequent to lymph node metastasis. The data shown are the mean±standard deviation ($p \leq 0.001$, n=3).

DETAILED DESCRIPTION

Figure 1:
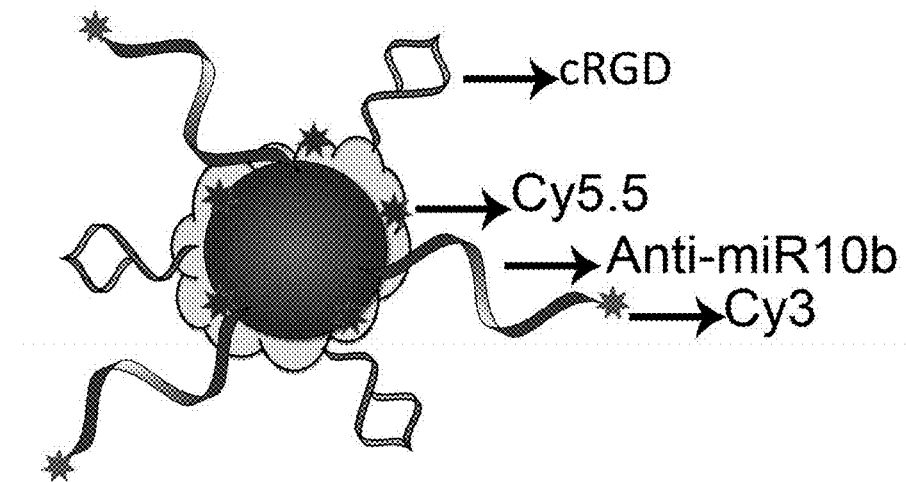
FIG. 1 is a diagram showing an exemplary therapeutic magnetic nanoparticle (MN-RGD-anti-miR-10b) having a dextran coating (light gray) and a covalently-attached tumor-targeting peptide (cRGD), fluorophore (Cy5.5), and a knock-down LNA oligonucleotide targeting human anti-miR-10b (anti-miR10b).

The therapeutic nanoparticles described herein were discovered to decrease cancer cell invasion and cancer metastasis in a mammal. Therapeutic nanoparticles having these activities are provided herein as well as methods of decreasing cancer cell invasion or metastasis in a subject and methods of treating a metastatic cancer in a lymph node in a subject by administering these therapeutic nanoparticles.

Compositions

Provided herein are therapeutic nanoparticles that have a diameter of between about 2 nm to about 200 nm (e.g., between about 10 nm to about 30 nm, between about 5 nm to about 25 nm, between about 10 nm to about 25 nm, between about 15 nm to about 25 nm, between about 20 nm and about 25 nm, between about 25 nm to about 50 nm, between about 50 nm and about 200 nm, between about 70 nm and about 200 nm, between about 80 nm and about 200 nm, between about 100 nm and about 200 nm, between about 140 nm to about 200 nm, and between about 150 nm to about 200 nm), and contain a polymer coating, and a nucleic acid containing at least 10 (e.g., at least 11, 12, 13, 14, 15, 16, 17, 18, 19, 20, or 21) contiguous nucleotides within the sequence of of GTGTAACACGTCTATACGC-CCA (SEQ ID NO: 17), ATGGGACATCTTGGCT-TAAACAC (SEQ ID NO: 1) or TGTCTAAGCTAAGAT CCCCTTA (SEQ ID NO: 2) that is covalently linked to the nanoparticle. In some embodiments, the therapeutic nanoparticles can contain a sequence that is complementary to at least 10 (e.g., at least 11,12,13,14,15,16,17,18,19,20,21,22, or 23) contiguous nucleotides within the sequence of precursor miR-10b (e.g., CCAGAGGUUGUAACGUUGUC-UAUAUAUACCCUGUAGAACCGAAUUUGUGU GGUAUCCGUAUAGUCACAGAUUCGAUUC-UAGGGGAAUAUAUGGUCGAUGC AAAAACUUCA; SEQ ID NO: 20). Mature and precursor miR-10b are also described in WO 07/073737, U.S. Patent Application Publication No. 2011/0107440, Ma et al. (Breast Cancer Res. 12:210,2010), Li et al. (Cancer Lett. 299:29-36,2010), Ma et al. (Nat. Biotech. 28:341-347,2010), and Ma et al. (Nature 449:682-688, 2007) (each of which is incorporated by reference in its entirety).

Alternatively, the nucleic acid contained in the therapeutic nanoparticles can contain a sequence that is complementary to a sequence of at least 10 (e.g., at least 11, 12, 13, 14, 15, 16, 17, 18, 19, 20, 21, 22, or 23) contiguous nucleotides present with a nucleic acid encoding an anti-apoptotic protein selected from the group of: survivin, XIAP, BCL2, BCL-XL, Mcl-1, Bfl-1, Bcl-W, Bcl-B, BRE, SGK1, MKP1/DUSP1, c-FLIP, MCL-1, MMP-15, BAG3, BIRC2, TRAP1, SCC-S2, HSP27, Livin, B7-H1, AAC-11, REG-1α, and HAX1. Alternatively, the nucleic acid contained in the therapeutic nanoparticles can contain a sequence that is complementary to a sequence of at least 10 (e.g., at least 11, 12, 13, 14, 15, 16, 17, 18, 19, 20, 21, 22, or 23) contiguous nucleotides present within mature human miR-21 or miR-125b.

In some embodiments, the therapeutic nanoparticles provided herein can be spherical or ellipsoidal, or can have an amorphous shape. In some embodiments, the therapeutic nanoparticles provided herein can have a diameter (between any two points on the exterior surface of the therapeutic nanoparticle) of between about 2 nm to about 200 nm (e.g., between about 10 nm to about 200 nm, between about 2 nm to about 30 nm, between about 5 nm to about 25 nm, between about 10 nm to about 25 nm, between about 15 nm to about 25 nm, between about 20 nm to about 25 nm, between about 50 nm to about 200 nm, between about 70 nm to about 200 nm, between about 80 nm to about 200 nm, between about 100 nm to about 200 nm, between about 140 nm to about 200 nm, and between about 150 nm to about 200 nm). In some embodiments, therapeutic nanoparticles having a diameter of between about 2 nm to about 30 nm localize to the lymph nodes in a subject. In some embodiments, therapeutic nanoparticles having a diameter of between about 40 nm to about 200 nm localize to the liver.

In some embodiments, the compositions can contain a mixture of two or more of the different therapeutic nanoparticles described herein. In some embodiments, the compositions contain at least one therapeutic nanoparticle containing at least 10 contiguous nucleotides within the sequence of SEQ ID NO: 1 or SEQ ID NO: 2 covalently linked to the nanoparticle (a nanoparticle for decrease miR-10b levels in a target cell), and at least one therapeutic nanoparticle containing a sequence that is complementary to a sequence of at least 10 contiguous nucleotides present within any one of SEQ ID NOS: 5-10 or within a nucleic acid encoding an anti-apoptotic protein (e.g., any of the anti-apoptotic proteins described herein).

In some embodiments, the therapeutic nanoparticles can be magnetic (e.g., contain a core of a magnetic material).

Nanoparticles

In some embodiments, any of the therapeutic nanoparticles described herein can contain a core of a magnetic material (e.g., a therapeutic magnetic nanoparticle). In some embodiments, the magnetic material or particle can contain a diamagnetic, paramagnetic, superparamagnetic, or ferromagnetic material that is responsive to a magnetic field. Non-limiting examples of therapeutic magnetic nanoparticles contain a core of a magnetic material containing a metal oxide selected from the group of: magnetite; ferrites (e.g., ferrites of manganese, cobalt, and nickel); Fe(II) oxides, and hematite, and metal alloys thereof. The core of magnetic material can be formed by converting metal salts to metal oxides using methods known in the art (e.g., Kieslich et al., *Inorg. Chem.* 2011). In some embodiments, the nanoparticles contain cyclodextrin gold or quantum dots. Non-limiting examples of methods that can be used to generate therapeutic magnetic nanoparticles are described in Medarova et al., *Methods Mol. Biol.* 555:1-13, 2009; and Medarova et al., *Nature Protocols* 1:429-431, 2006. Additional magnetic materials and methods of making magnetic materials are known in the art. In some embodiments of the methods described herein, the position or localization of therapeutic magnetic nanoparticles can be imaged in a subject (e.g., imaged in a subject following the administration of one or more doses of a therapeutic magnetic nanoparticle).

In some embodiments, the therapeutic nanoparticles described herein do not contain a magnetic material. In some embodiments, a therapeutic nanoparticle can contain, in part, a core of containing a polymer (e.g., poly(lactic-co-glycolic acid)). Skilled practitioners will appreciated that any number of art known materials can be used to prepare nanoparticles, including, but are not limited to, gums (e.g., Acacia, Guar), chitosan, gelatin, sodium alginate, and albumin. Additional polymers that can be used to generate the therapeutic nanoparticles described herein are known in the art. For example, polymers that can be used to generate the therapeutic nanoparticles include, but are not limited to, cellulosics, poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides, polyorthoesters, polycyanoacrylate and polycaprolactone.

Skilled practitioners will appreciate that the material used in the composition of the nanoparticles, the methods for preparing, coating, and methods for controlling the size of the nanoparticles can vary substantially. However, these methods are well known to those in the art. Key issues include the biodegradability, toxicity profile, and pharmacokinetics/pharmacodynamics of the nanoparticles. The composition and/or size of the nanoparticles are key determinants of their biological fate. For example, larger nanoparticles are typically taken up and degraded by the liver, whereas smaller nanoparticles (<30 nm in diameter) typically circulate for a long time (sometimes over 24-hr blood half-life in humans) and accumulate in lymph nodes and the interstitium of organs with hyperpermeable vasculature, such as tumors.

Polymer Coatings

The therapeutic nanoparticles described herein contain a polymer coating over the core magnetic material (e.g., over the surface of a magnetic material). The polymer material can be suitable for attaching or coupling one or more biological agents (e.g., such as any of the nucleic acids, fluorophores, or targeting peptides described herein). One of more biological agents (e.g., a nucleic acid, fluorophore, or targeting peptide) can be fixed to the polymer coating by chemical coupling (covalent bonds).

In some embodiments, the therapeutic nanoparticles are formed by a method that includes coating the core of magnetic material with a polymer that is relatively stable in water. In some embodiments, the therapeutic nanoparticles are formed by a method that includes coating a magnetic material with a polymer or absorbing the magnetic material into a thermoplastic polymer resin having reducing groups thereon. A coating can also be applied to a magnetic material using the methods described in U.S. Pat. Nos. 5,834,121, 5,395,688, 5,356,713, 5,318,797, 5,283,079, 5,232,789, 5,091,206, 4,965,007, 4,774,265, 4,770,183, 4,654,267, 4,554,088, 4,490,436, 4,336,173, and 4,421,660; and WO 10/111066 (each disclosure of which is incorporated herein by reference).

Method for the synthesis of iron oxide nanoparticles include, for example, physical and chemical methods. For example, iron oxides can be prepared by co-precipitation of Fe2+ and Fe3+ salts in an aqueous solution. The resulting core consists of magnetite ($Fe_3O_4$), maghemite ($\gamma$-$Fe_2O_3$) or a mixture of the two. The anionic salt content (chlorides, nitrates, sulphates etc), the Fe2+ and Fe3+ ratio, pH and the ionic strength in the aqueous solution all play a role in controlling the size. It is important to prevent the oxidation of the synthesized nanoparticles and protect their magnetic properties by carrying out the reaction in an oxygen free environment under inert gas such as nitrogen or argon. The coating materials can be added during the co-precipitation process in order to prevent the agglomeration of the iron oxide nanoparticles into microparticles. Skilled practitioners will appreciated that any number of art known surface coating materials can be used for stabilizing iron oxide nanoparticles, among which are synthetic and natural polymers, such as, for example, polyethylene glycol (PEG), dextran, polyvinylpyrrolidone (PVP), fatty acids, polypeptides, chitosin, gelatin.

For example, U.S. Pat. No. 4,421,660 note that polymer coated particles of an inorganic material are conventionally prepared by (1) treating the inorganic solid with acid, a combination of acid and base, alcohol or a polymer solution; (2) dispersing an addition polymerizable monomer in an aqueous dispersion of a treated inorganic solid and (3) subjecting the resulting dispersion to emulsion polymerization conditions. (col. 1, lines 21-27) U.S. Pat. No. 4,421,660 also discloses a method for coating an inorganic nanoparticles with a polymer, which comprises the steps of (1) emulsifying a hydrophobic, emulsion polymerizable monomer in an aqueous colloidal dispersion of discrete particles of an inorganic solid and (2) subjecting the resulting emulsion to emulsion polymerization conditions to form a stable, fluid aqueous colloidal dispersion of the inorganic solid particles dispersed in a matrix of a water-insoluble polymer of the hydrophobic monomer (col. 1, lines 42-50).

Alternatively, polymer-coated magnetic material can be obtained commercially that meets the starting requirements of size. For example, commercially available ultrasmall superparamagnetic iron oxide nanoparticles include NC100150 Injection (Nycomed Amersham, Amersham Health) and Ferumoxytol (AMAG Pharmaceuticals, Inc.).

Suitable polymers that can be used to coat the core of magnetic material include without limitation: polystyrenes, polyacrylamides, polyetherurethanes, polysulfones, fluorinated or chlorinated polymers such as polyvinyl chloride, polyethylenes, and polypropylenes, polycarbonates, and polyesters. Additional examples of polymers that can be used to coat the core of magnetic material include polyolefins, such as polybutadiene, polydichlorobutadiene, polyisoprene, polychloroprene, polyvinylidene halides, polyvinylidene carbonate, and polyfluorinated ethylenes. A number of copolymers, including styrene/butadiene, alpha-methyl styrene/dimethyl siloxane, or other polysiloxanes can also be used to coat the core of magnetic material (e.g., polydimethyl siloxane, polyphenylmethyl siloxane, and polytrifluoropropylmethyl siloxane). Additional polymers that can be used to coat the core of magnetic material include polyacrylonitriles or acrylonitrile-containing polymers, such as poly alpha-acrylanitrile copolymers, alkyd or terpenoid resins, and polyalkylene polysulfonates. In some embodiments, the polymer coating is dextran.

Nucleic Acids

The therapeutic nanoparticles provided contain at least one nucleic acid containing at least 10 (e.g., at least 11, 12, 13, 14, 15, 16, 17, 18, 19, 20, 21, or 22) contiguous nucleotides within SEQ ID NO: 17, SEQ ID NO: 1 or SEQ ID NO: 2 that is covalently-linked to the nanoparticle. In some embodiments, the nucleic acid contains the sequence of SEQ ID NO: 17, SEQ ID NO: 1 or SEQ ID NO: 2. In some embodiments, the nucleic acid can contain a sequence of at least 10 (e.g., 11, 12, 13, 14, 15, 16, 17, 18, 19, 20, 21, 22, or 23) contiguous nucleotides that is complementary to a sequence within a nucleic acid encoding an anti-apoptotic protein selected from the group of: survivin, XIAP, BCL2, BCL-XL, Mcl-1, Bfl-1, Bcl-W, Bcl-B, BRE, SGK1, MKP1/DUSP1, c-FLIP, MCL-1, MMP-15, BAG3, BIRC2, TRAP1, SCC-S2, HSP27, Livin, B7-H1, AAC-11, REG-1$\alpha$, and HAX1. In some embodiments, the covalently-linked nucleic acid molecule contains a sequence that is complementary to all or part of an mRNA encoding an anti-apoptotic protein (e.g., any of the anti-apoptotic proteins described herein). For example, the covalently-linked nucleic acid can be complementary to all or part of a non-coding region of the coding strand of a nucleotide sequence encoding an anti-apoptotic protein (e.g., any of the anti-apoptotic proteins described herein). Non-coding regions ("5' and 3' untranslated regions") are the 5' and 3' sequences that flank the coding region in a gene and are not translated into amino acids. In some embodiments, the nucleic acid covalently-linked to the therapeutic nanoparticle is complementary to the translational start codon or a sequence encoding amino acids 1 to 5 of an anti-apoptotic protein (e.g., any of the anti-apoptotic proteins described herein).

In some embodiments, the nucleic acid contained in the therapeutic nanoparticles can contain a sequence of at least 10 (e.g., at least 11, 12, 13, 14, 15, 16, 17, 18, 19, 20, 21, 22, or 23) contiguous nucleotides within a sequence complementary to mature human miR-21 or miR-125b. Mature human miR-125b has a sequence of ucccugagacccua acuuguga (SEQ ID NO: 5), ucccugagacccuaacuuguga (SEQ ID NO: 6), ucccugagacccu aacuuguga (SEQ ID NO: 7), or ucacaagucaggcucuugggac (SEQ ID NO: 8). Mature human miR-21 has a sequence of cauugcacuugucucggucuga (SEQ ID NO: 9) or aggcggagacuugggcaauug (SEQ ID NO: 10).

The attached nucleic acid can be single-stranded or double-stranded. In some embodiments, the nucleic acid contains the sequence of SEQ ID NO: 1 and has a total length of between 23 nucleotides and 50 nucleotides (e.g., between 23-30 nucleotides, between 30-40 nucleotides, and between 40-50 nucleotides). In some embodiments, the nucleic acid contains the sequence of SEQ ID NO: 2 and has a total length of between 22 nucleotides and 50 nucleotides (e.g., between 22-30 nucleotides, between 30-40 nucleotides, and between 40-50 nucleotides). In some embodiments, the nucleic acid can be an antisense RNA, a siRNA, or a ribozyme.

Antisense nucleic acid molecules can be covalently linked to the therapeutic nanoparticles described herein. For example, nucleic acid sequences that contain a portion of the sequence (at least 10 nucleotides) within SEQ ID NO: 1 are complementary to the sequence of mature human miR-10b (uacccuguagaaccgaauuugug; SEQ ID NO: 3), and nucleic acid sequences that contain at least a portion of the sequence (e.g., at least 10 nucleotides) within SEQ ID NO: 2 are complementary to the sequence of the minor form of mature human miR-10b (acagauucgauucuagggaau; SEQ ID NO: 4). In some embodiments nucleic acid sequences that contain a portion of the sequence (at least 10 nucleotides) within SEQ ID NO: 17 target human miR-10b for down-regulation.

Based upon the sequences provided herein (e.g., the sequences for mature human miR-10b; SEQ ID NO: 3 and SEQ ID NO: 4; and the sequence precursor miR-10b; SEQ ID NO: 20), one of skill in the art can easily choose and synthesize any of a number of appropriate antisense molecules (e.g., antisense molecules to target mature human miR-10b). For example, an antisense nucleic acid that targets miR-10b can contain a sequence complementary to at least 10 (e.g., at least 15 or 20) contiguous nucleotides present in SEQ ID NO: 3 or SEQ ID NO: 4 or 20, or a sequence for miR-10b known in the art.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or modified nucleotides (e.g., any of the modified oligonucleotides described herein) designed to increase the biological stability of the molecules or to increase the physical stability of the duplex formed between the antisense and sense nucleic acids, e.g., phosphorothioate derivatives and acridine-substituted nucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest). In some embodiments, the antisense nucleic acid molecules described herein can hybridize to a target nucleic acid by conventional nucleotide complementarities and form a stable duplex.

An antisense nucleic acid molecule can be an α-anomeric nucleic acid molecule. An α-anomeric nucleic acid molecule forms specific double-stranded hybrids with complementary RNA in which, contrary to the usual β-units, the strands run parallel to each other (Gaultier et al., *Nucleic Acids Res.* 15:6625-6641, 1987). The antisense nucleic acid molecule can also comprise a 2'-O-methylribonucleotide (Inoue et al., *Nucleic Acids Res.*, 15:6131-6148, 1987) or a chimeric RNA-DNA analog (Inoue et al., *FEBS Lett.* 215:327-330, 1987).

In some embodiments, the nucleic acid is a ribozyme. For example, in some embodiments the nucleic acid is a ribozyme that has specificity for mature human miR-10b in the cell (SEQ ID NO: 1 or 2). Ribozymes are catalytic RNA molecules with ribonuclease activity that are capable of cleaving a single-stranded nucleic acid, such as an RNA, to which they have a complementary region. Thus, ribozymes (e.g., hammerhead ribozymes (described in Haselhoff et al. *Nature* 334:585-591, 1988)) can be used to catalytically cleave RNA. A ribozyme having specificity for mature human miR-10b can be designed based upon the nucleotide sequence of SEQ ID NO: 1 or SEQ ID NO: 2. For example, a derivative of a Tetrahymena L-19 IVS RNA can be constructed in which the nucleotide sequence of the active site is complementary to the nucleotide sequence to be cleaved (complementary to SEQ ID NO: 1 or SEQ ID NO: 2, or any other contiguous sequence of at least 10 nucleotides in the miRNA-10b precursor) (U.S. Pat. Nos. 4,987, 071 and 5,116,742). Alternatively, an oligonucleotide containing the sequence of SEQ ID NO: 1, SEQ ID NO: 2, or SEQ ID NO: 17 can be used to select a catalytic RNA having a specific ribonuclease activity from a pool of RNA molecules. See, e.g., Bartel et al. *Science* 261:1411-1418, 1993.

In some embodiments, the nucleic acid is a small interfering RNA (siRNA). RNAi is a process in which RNA is degraded in host cells. To decrease expression of an RNA, double-stranded RNA (dsRNA) containing a sequence corresponding to a portion of the target RNA (e.g., mature human miR-10b) is introduced into a cell. The dsRNA is digested into 21-23 nucleotide-long duplexes called short interfering RNAs (or siRNAs), which bind to a nuclease complex to form what is known as the RNA-induced silencing complex (or RISC). The RISC targets the endogenous target RNA by base pairing interactions between one of the siRNA strands and the endogenous RNA. It then cleaves the endogenous RNA about 12 nucleotides from the 3' terminus of the siRNA (see Sharp et al., *Genes Dev.* 15:485-490, 2001, and Hammond et al., *Nature Rev. Gen.* 2:110-119, 2001).

Standard molecular biology techniques can be used to generate siRNAs. Short interfering RNAs can be chemically synthesized, recombinantly produced, e.g., by expressing RNA from a template DNA, such as a plasmid, or obtained from commercial vendors such as Dharmacon. The RNA used to mediate RNAi can include modified nucleotides (e.g., any of the modified nucleotides described herein), such as phosphorothioate nucleotides. The siRNA molecules used to decrease the levels of mature human miR-10b can vary in a number of ways. For example, they can include a 3' hydroxyl group and strands of 21, 22, or 23 consecutive nucleotides. They can be blunt ended or include an overhanging end at either the 3' end, the 5' end, or both ends. For example, at least one strand of the RNA molecule can have a 3' overhang from about 1 to about 6 nucleotides (e.g., 1-5, 1-3, 2-4 or 3-5 nucleotides (whether pyrimidine or purine nucleotides) in length. Where both strands include an overhang, the length of the overhangs may be the same or different for each strand.

To further enhance the stability of the RNA duplexes, the 3' overhangs can be stabilized against degradation (by, e.g., including purine nucleotides, such as adenosine or guanosine nucleotides, or replacing pyrimidine nucleotides with modified nucleotides (e.g., substitution of uridine two-nucleotide 3' overhangs by 2'-deoxythymidine is tolerated and does not affect the efficiency of RNAi). Any siRNA can be used provided it has sufficient homology to the target of interest. There is no upper limit on the length of the siRNA that can be used (e.g., the siRNA can range from about 21-50, 50-100, 100-250, 250-500, or 500-1000 base pairs).

In some embodiments, the nucleic acid molecule can contain at least one modified nucleotide (a nucleotide containing a modified base or sugar). In some embodiments, the nucleic acid molecule can contain at least one modification in the phosphate (phosphodiester) backbone. The introduction of these modifications can increase the stability, or improve the hybridization or solubility of the nucleic acid molecule. The molecules described herein can contain one or more (e.g., two, three, four, of five) modified nucleotides. The modified nucleotides can contain a modified base or a modified sugar. Non-limiting examples of modified bases include: 8-oxo-$N^6$-methyladenine, 7-deazaxanthine, 7-deazaguanine, $N^4$, $N^4$-ethanocytosin, $N^6$, $N^6$-ethano-2,6-diaminopurine, 5-($C^3$-$C^6$)-alkynyl-cytosine, pseudoisocytosine, 2-hydroxy-5-methyl-4-triazolopyridin, isocytosine, isoguanine, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-i sopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

Additional non-limiting examples of modified bases include those nucleobases described in U.S. Pat. Nos. 5,432,272 and 3,687,808 (herein incorporated by reference), Freier et al., *Nucleic Acid Res.* 25:4429-4443, 1997; Sanghvi, Antisense Research and Application, Chapter 15, Ed. S. T. Crooke and B. Lebleu, CRC Press, 1993; Englisch, et al., *Angewandte Chemie* 30:613-722, 1991, Kroschwitz, Concise Encyclopedia of Polymer Science and Engineering, John Wiley & Sons, pp. 858-859, 1990; and Cook, *Anti-Cancer Drug Design* 6:585-607, 1991. Additional non-limiting examples of modified bases include universal bases (e.g., 3-nitropyrole and 5-nitroindole). Other modified bases include pyrene and pyridyloxazole derivatives, pyrenyl, pyrenylmethylglycerol derivatives, and the like. Other preferred universal bases include pyrrole, diazole, or triazole derivatives, including those universal bases known in the art.

In some embodiments, the modified nucleotide can contain a modification in its sugar moiety. Non-limiting examples of modified nucleotides that contain a modified sugar are locked nucleotides (LNAs). LNA monomers are described in WO 99/14226 and U.S. Patent Application Publications Nos. 20110076675, 20100286044, 20100279895, 20100267018, 20100261175, 20100035968, 20090286753, 20090023594, 20080096191, 20030092905, 20020128381, and 20020115080 (herein incorporated by reference). Additional non-limiting examples of LNAs are disclosed in U.S. Pat. Nos. 6,043,060, 6,268,490, WO 01/07455, WO 01/00641, WO 98/39352, WO 00/56746, WO 00/56748, and WO 00/66604 (herein incorporated by reference), as well as in Morita et al., *Bioorg. Med. Chem. Lett.* 12(1):73-76, 2002; Hakansson et al., *Bioorg. Med. Chem. Lett.* 11(7):935-938, 2001; Koshkin et al., *J. Org. Chem.* 66(25):8504-8512, 2001; Kvaerno et al., *J. Org. Chem.* 66(16):5498-5503, 2001; Hakansson et al., *J. Org. Chem.* 65(17):5161-5166, 2000; Kvaerno et al., *J. Org. Chem.* 65(17):5167-5176, 2000; Pfundheller et al., *Nucleosides Nucleotides* 18(9):2017-2030, 1999; and Kumar et al., *Bioorg. Med. Chem. Lett.* 8(16):2219-2222, 1998. In some embodiments, the modified nucleotide is an oxy-LNA monomer, such as those described in WO 03/020739.

Modified nucleotides can also include antagomirs (2'-O-methyl-modified, cholesterol-conjugated single stranded RNA analogs); ALN (α-L-LNA); ADA (2'-N-adamantylmethylcarbonyl-2'-amino-LNA); PYR (2'-N-pyrenyl-1-methyl-2'-amino-LNA); OX (oxetane-LNA); ENA (2'-O, 4''-C-ethylene bridged nucleic acid); AENA (2'-deoxy-2'-N, 4'-C-ethylene-LNA); CLNA (2',4'-carbocyclic-LNA); and CENA (2',4'-carbocyclic-ENA); HM-modified DNAs (4'-C-hydroxymethyl-DNA); 2'-substituted RNAs (with 2'-O-methyl, 2'-fluoro, 2'-aminoethoxymethyl, 2'-aminopropoxymethyl, 2'-aminoethyl, 2'-guanidinoethyl, 2'-cyanoethyl, 2'-aminopropyl); and RNAs with radical modifications of the ribose sugar ring, such as Unlocked Nucleic Acid (UNA), Altritol Nucleic Acid (ANA) and Hexitol Nucleic Acid (HNA) (see, Bramsen et al., *Nucleic Acids Res.* 37:2867-81, 2009).

The molecules described herein can also contain a modification in the phosphodiester backbone. For example, at least one linkage between any two contiguous (adjoining) nucleotides in the molecule can be connected by a moiety containing 2 to 4 groups/atoms selected from the group of: —$CH_2$—, —O—, —S—, —$NR^H$—, >C=O, >C=$NR^H$, >C=S, —Si(R")$_2$—, —SO—, —S(O)$_2$—, —P(O)$_2$—, —PO(BH$_3$)—, P(O,S)—, —P(S)$_2$—, —PO(R")—, —PO(OCH$_3$)—, and —PO(NHR$^H$)—, where $R^H$ is selected from hydrogen and $C_{1-4}$-alkyl, and R" is selected from $C_{1-6}$-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH=(including $R^5$ when used as a linkage to a succeeding monomer), —$CH_2$—$CH_2$—O—, —$NR^H$—$CH_2$—$CH_2$—, —$CH_2$—$CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$—, —O—CO—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N=(including $R^5$ when used as a linkage to a succeeding monomer), —$CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$—, —O—$CH_2$—S—, —S—$CH_2$—O—, —$CH_2$—$CH_2$—S—, —O—$CH_2$—$CH_2$—S—, —S—$CH_2$—CH=(including $R^5$ when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —O—S(O)$_2$—O—, —O—S(O)$_2$—$CH_2$—, —O—S(O)$_2$—$NR^H$—, —$NR^H$—S(O)$_2$—$CH_2$—, —O—S(O)$_2$—$CH_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(OCH$_2$CH$_3$)—O—, —O—PO(OCH$_2$S—R)—O—, —O—PO(BH$_3$)—O—, —O—PO(NHR$^N$)—O—, —O—P(O)$_2$—$NR^H$—, —$NR^H$—P(O)$_2$—O—, —O—P(O,NR$^H$)2-O—, —$CH_2$—P(O)$_2$—O—, —O—P(O)$_2$—$CH_2$—, and —O—Si(R")$_2$—O—; among which —$CH_2$—CO—$NR^H$—, —$CH_2$—$NR^H$—O—, —S—$CH_2$—O—, —O—P(O)$_2$—O—, —O—P(O,S)—O—, —O—P(S)$_2$—O—, —$NR^H$—P(O)$_2$—O—, —O—P(O,NR$^H$)—O—, —O—PO(R")—O—, —O—PO(CH$_3$)—O—, and —O—PO(NHR$^N$)—O—, where $R^H$ is selected form hydrogen and $C_{1-4}$-alkyl, and R" is selected from $C_{1-6}$-alkyl and phenyl. Further illustrative examples are given in Mesmaeker et. al., *Curr. Opin. Struct. Biol.* 5:343-355, 1995; and Freier et al., *Nucleic Acids Research* 25:4429-43, 1997. The left-hand side of the internucleoside linkage is bound to the 5-membered ring as substituent P* at the 3'-position, whereas the right-hand side is bound to the 5'-position of a preceding monomer.

In some embodiments, the deoxyribose phosphate backbone of the nucleic acid can be modified to generate peptide nucleic acids (see Hyrup et al., *Bioorganic & Medicinal Chem.* 4(1): 5-23, 1996). Peptide nucleic acids (PNAs) are nucleic acid mimics, e.g., DNA mimics, in which the deoxyribose phosphate backbone is replaced by a pseudopeptide backbone and only the four natural nucleobases are retained. The neutral backbone of PNAs allows for specific hybridization to DNA and RNA under conditions of low ionic strength. The synthesis of PNA oligomers can be performed using standard solid phase peptide synthesis protocols, e.g., as described in Hyrup et al., 1996, supra; Perry-O'Keefe et al., *Proc. Natl. Acad. Sci. U.S.A.* 93:14670-675, 1996.

PNAs can be modified, e.g., to enhance their stability or cellular uptake, by attaching lipophilic or other helper groups to PNA, by the formation of PNA-DNA chimeras, or by the use of liposomes or other techniques of delivery known in the art. For example, PNA-DNA chimeras can be generated which may combine the advantageous properties of PNA and DNA. Such chimeras allow DNA recognition enzymes, e.g., RNAse H, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup, 1996, supra, and Finn et al., *Nucleic Acids Res.* 24:3357-63, 1996. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., *Nucleic Acids Res.,* 17:5973-88, 1989). PNA monomers are then coupled in a stepwise manner to produce a chimeric molecule with a 5' PNA segment and a 3' DNA segment (Finn et al., *Nucleic Acids Res.* 24:3357-63, 1996). Alternatively, chimeric molecules can be synthesized with a 5' DNA segment and a 3' PNA segment (Peterser et al., *Bioorganic Med. Chem. Lett.* 5:1119-11124, 1975).

In some embodiments, any of the nucleic acids described herein can be modified at either the 3' or 5' end (depending on how the nucleic acid is covalently-linked to the therapeutic nanoparticle) by any type of modification known in the art. For example, either end may be capped with a protecting group, attached to a flexible linking group, or attached to a reactive group to aid in attachment to the substrate surface (the polymer coating). Non-limiting examples of 3' or 5' blocking groups include: 2-amino-2-oxyethyl, 2-aminobenzoyl, 4-aminobenzoyl, acetyl, acetyloxy, (acetylamino)methyl, 3-(9-acridinyl), tricyclo[3.3.1.1(3,7)]dec-1-yloxy, 2-aminoethyl, propenyl, (9-anthracenylmethoxy)carbonyl, (1,1-dmimethylpropoxy)carbonyl, (1,1-dimethylpropoxy)carbonyl, [1-methyl-1-[4-(phenylazo)phenyl]ethoxy]carbonyl, bromoacetyl, (benzoylamino)methyl, (2-bromoethoxy)carbonyl, (diphenylmethoxy)carbonyl, 1-methyl-3-oxo-3-phenyl-1-propenyl, (3-bromo-2-nitrophenyl)thio, (1,1-dimethyl ethoxy)carbonyl, [[(1,1-di methylethoxy)carbonyl] amino] ethyl, 2-(phenylmethoxy)phenoxy, (1=[1,1'-biphenyl]-4-yl-1-methylethoxy) carbonyl, bromo, (4-bromophenyl)sulfonyl, 1H-benzotriazol-1-yl, [(phenylmethyl) thio]carbonyl, [(phenymetyl)thio]methyl, 2-methylpropyl, 1,1-dimethylethyl, benzoyl, diphenylmethyl, phenylmethyl, carboxyacetyl, aminocarbonyl, chlorodifluoroacetyl, trifluoromethyl, cyclohexylcarbonyl, cycloheptyl, cyclohexyl, cyclohexylacetyl, chloro, carboxymethyl, cyclopentylcarbonyl, cyclopentyl, cyclopropylmethyl, ethoxycarbonyl, ethyl, fluoro, formyl, 1-oxohexyl, iodo, methyl, 2-methoxy-2-oxoethyl, nitro, azido, phenyl, 2-carboxybenzoyl, 4-pyridinylmethyl, 2-piperidinyl, propyl, 1-methylethyl, sulfo, and ethenyl. Additional examples of 5' and 3' blocking groups are known in the art. In some embodiments, the 5' or 3' blocking groups prevent nuclease degradation of the molecule.

The nucleic acids described herein can be synthesized using any methods known in the art for synthesizing nucleic acids (see, e.g., Usman et al., *J. Am. Chem. Soc.* 109:7845, 1987; Scaringe et al., *Nucleic Acid Res.* 18:5433, 1990; Wincott et al., *Methods Mol. Biol.* 74:59, 1997; and Milligan, *Nucleic Acid Res.* 21:8783, 1987). These typically make use of common nucleic acid protecting and coupling groups. Synthesis can be performed on commercial equipment designed for this purpose, e.g., a 394 Applied Biosystems, Inc. synthesizer, using protocols supplied by the manufacturer. Additional methods for synthesizing the molecules described herein are known in the art. Alternatively, the nucleic acids can be specially ordered from commercial vendors that synthesize oligonucleotides.

In some embodiments, the nucleic acid is attached to the therapeutic nanoparticle at its 5' end. In some embodiments, the nucleic acid is attached to the therapeutic nanoparticle at its 3' end. In some embodiments, the nucleic acid is attached to the therapeutic nanoparticle through a base present in the nucleic acid.

In some embodiments, the nucleic acid (e.g., any of the nucleic acids described herein) is attached to the therapeutic nanoparticle (e.g., to the polymer coating of the therapeutic nanoparticle) through a chemical moiety that contains a thioether bond or a disulfide bond. In some embodiments, the nucleic acid is attached to the therapeutic nanoparticle through a chemical moiety that contains an amide bond. Additional chemical moieties that can be used to covalently link a nucleic acid to a therapeutic nanoparticle are known in the art.

A variety of different methods can be used to covalently link a nucleic acid to a therapeutic nanoparticle. Non-limiting examples of methods that can be used to link a nucleic acid to a magnetic particle are described in EP 0937097; US RE41005; Lund et al., *Nucleic Acid Res.* 16:10861, 1998; Todt et al., *Methods Mol. Biol.* 529:81-100, 2009; Brody et al., *J. Biotechnol.* 74:5-13, 2000; Ghosh et al., *Nucleic Acids Res.* 15:5353-5372, 1987; U.S. Pat. Nos. 5,900,481; 7,569,341; 6,995,248; 6,818,394; 6,811,980; 5,900,481; and 4,818,681 (each of which is incorporated by reference in its entirety). In some embodiments, carboiimide is used for the end-attachment of a nucleic acid to a therapeutic nanoparticle. In some embodiments, the nucleic acid is attached to the therapeutic nanoparticle through the reaction of one of its bases with an activated moiety present on the surface of the therapeutic nanoparticle (e.g., the reaction of an electrophilic base with a nucleophilic moiety on the surface of the therapeutic nanoparticle, or the reaction of a nucleophilic base with a electrophilic residue on the surface of the therapeutic nanoparticle). In some embodiments, a 5'-NH$_2$ modified nucleic acid is attached to a therapeutic nanoparticle containing CNBr-activated hydroxyl groups (see, e.g., Lund et al., supra). Additional methods for attaching an amino-modified nucleic acid to a therapeutic nanoparticle are described below. In some embodiments, a 5'-phosphate nucleic acid is attached to a therapeutic nanoparticle containing hydroxyl groups in the presence of a carbodiimide (see, e.g., Lund et al., supra).

Other methods of attaching a nucleic acid to a therapeutic nanoparticle include carboiimide-mediated attachment of a 5'-phosphate nucleic acid to a $NH_2$ group on a therapeutic nanoparticle, and carboiimide-mediated attachment of a 5'-$NH_2$ nucleic acid to a therapeutic nanoparticle having carboxyl groups (see, e.g., Lund et al., supra).

In exemplary methods, a nucleic acid can be produced that contains a reactive amine or a reactive thiol group. The amine or thiol in the nucleic acid can be linked to another reactive group. The two common strategies to perform this reaction are to link the nucleic acid to a similar reactive moiety (amine to amine or thiol to thiol), which is called homobifunctional linkage, or to link to the nucleic acid to an opposite group (amine to thiol or thiol to amine), known as heterobifunctional linkage. Both techniques can be used to attach a nucleic acid to a therapeutic nanoparticle (see, for example, Misra et al., *Bioorg. Med. Chem. Lett.* 18:5217-5221, 2008; Mirsa et al., *Anal. Biochem.* 369:248-255, 2007; Mirsa et al., *Bioorg. Med. Chem. Lett.* 17:3749-3753, 2007; and Choithani et al., *Methods Mol Biol.* 381:133-163, 2007).

Traditional attachment techniques, especially for amine groups, have relied upon homobifunctional linkages. One of the most common techniques has been the use of bisaldehydes such as glutaraldehyde. Disuccinimydyl suberate (DSS), commercialized by Syngene (Frederick, Md.) as synthetic nucleic acid probe (SNAP) technology, or the reagent p-phenylene diisothiocyanate can also be used to generate a covalent linkage between the nucleic acid and the therapeutic nanoparticle. N,N'-o-phenylenedimaleimide can be used to cross-link thiol groups. With all of the homobifunctional cross-linking agents, the nucleic acid is initially activated and then added to the therapeutic nanoparticle (see, for example, Swami et al., *Int. J. Pharm.* 374:125-138, 2009, Todt et al., *Methods Mol. Biol.* 529:81-100, 2009; and Limanskiĭ, *Biofizika* 51:225-235, 2006).

Heterobifunctional linkers can also be used to attach a nucleic acid to a therapeutic nanoparticle. For example, N-succinidimidyl-3-(2-pyridyldithio)proprionate (SPDP) initially links to a primary amine to give a dithiol-modified compound. This can then react with a thiol to exchange the pyridylthiol with the incoming thiol (see, for example, Nostrum et al., *J. Control Release* 15; 153(1):93-102, 2011, and Berthold et al., *Bioconjug. Chem.* 21:1933-1938, 2010).

An alternative approach for thiol use has been a thiol-exchange reaction. If a thiolated nucleic acid is introduced onto a disulfide therapeutic nanoparticle, a disulfide-exchange reaction can occur that leads to the nucleic acid being covalently bonded to the therapeutic nanoparticle by a disulfide bond. A multitude of potential cross-linking chemistries are available for the heterobifunctional cross-linking of amines and thiols. Generally, these procedures have been used with a thiolated nucleotide. Reagents typically employed have been NHS (N-hydroxysuccinimide ester), MBS (m-maleimidobenzoyl-N-succinimide ester), and SPDP (a pyridyldisulfide-based system). The heterobifunctional linkers commonly used rely upon an aminated nucleic acid. Additional methods for covalently linking a nucleic acid to a therapeutic nanoparticle are known in the art.

Targeting Peptides

The therapeutic nanoparticles described herein can also contain at least one (e.g., two, three, or four) targeting peptide covalently-linked to the therapeutic nanoparticle. Targeting peptides can be used to deliver an agent (e.g., any of the therapeutic nanoparticles described herein) to a specific cell type or tissue. Targeting peptides often contain an amino acid sequence that is recognized by a molecule present on the surface of a cell (e.g., a cell type present in a target tissue). For example, a targeting peptide comprising an RGD peptide specifically binds to aVf3.3 integrin expressed in the plasma membrane of breast cancer cells. Additional non-limiting targeting peptides that can be covalently-linked to any of the therapeutic nanoparticles described herein include: an EPPT peptide, a contiguous sequence of amino acids (e.g., at least 10, 15, or 20) present within galectin-3, a contiguous sequence of amino acids (e.g., at least 10, 15, or 20) present within gonadotropin-releasing hormone, NYLHNHPYGTVG (SEQ ID NO: 11), SNPFSKPYGLTV (SEQ ID NO: 12), GLHESTFTQRRL (SEQ ID NO: 13), YPHYSLPGSSTL (SEQ ID NO: 14), SSLEPWHRTTSR (SEQ ID NO: 15), LPLALPRHNASV (SEQ ID NO: 16), βAla-(Arg)$_7$-Cys (SEQ ID NO: 19) (e.g., $C_{14}$-βAla-(Arg)$_7$-Cys), a contiguous sequence of amino acids (e.g., at least 10, 15, or 20) present within somatostatin, a contiguous sequence of amino acids (e.g., at least 10, 15, or 20) present within cholecystokinin-A, a contiguous sequence of amino acids (e.g., at least 10, 15, or 20) present within cholecystokinin-B, a contiguous sequence of amino acids (e.g., at least 10, 15, or 20) present within glucagon-like peptide-1, a contiguous sequence of amino acids (e.g., at least 10, 15, or 20) present in bombesin, a contiguous sequence of amino acids (e.g., at least 10, 15, or 20) present within neuropeptide-Y, a contiguous sequence of amino acids (e.g., at least 10, 15, or 20) present within vasoactive intestinal peptide, a contiguous sequence of amino acids (e.g., at least 10, 15, or 20) present within gastrin-1, a contiguous sequence of amino acids (e.g., at least 10, 15, or 20) present within neurotensin, a contiguous sequence of amino acids (e.g., at least 10, 15, or 20) present within vascular endothelial growth factor, a contiguous sequence of amino acids (e.g., at least 10, 15, or 20) present within endoglin, or a contiguous sequence of amino acids (e.g., at least 10, 15, or 20) present within epithelial growth factor. Additional examples of targeting peptides are described in U.S. Patent Application Publication No. 2008/00056998 (herein incorporated by reference in its entirety). Additional examples of targeting peptides are known in the art.

In some embodiments, the targeting peptide can be covalently linked to the therapeutic nanoparticle at its N-terminus or at its C-terminus. In some embodiments, the targeting peptide can be covalently linked to the therapeutic nanoparticle through an amino acid side chain.

Targeting peptides can be covalently-linked to any of the therapeutic nanoparticles described herein through a chemical moiety containing a disulfide bond, an amide bond, or a thioether bond. Additional chemical moieties that can be used to covalently link a targeting peptide to a therapeutic nanoparticle are known in the art.

A variety of different methods can be used to covalently link a targeting peptide to a therapeutic nanoparticle. Non-limiting examples of methods of covalently linking a targeting peptide to a therapeutic nanoparticle are described in Hofmann et al., *Proc. Nat. Acad. Sci. U.S.A.* 10:3516-3518, 2007; Chan et al., *PLoS ONE* 2(11): e1164, 2007; U.S. Pat. No. 7,125,669; U.S. Patent Application Publication No. 20080058224; U.S. Patent Application Publication No. 20090275066; and Mateo et al., *Nature Protocols* 2:1022-1033, 2007 (each of which are incorporated by reference in their entirety). In some embodiments, the therapeutic nanoparticle can be activated for attachment with a targeting peptide, for example in non-limiting embodiments, the therapeutic nanoparticle can be epoxy-activated, carboxyl-activated, iodoacetyl-activated, aldehyde-terminated, amine-terminated, or thiol-activated. Additional methods for covalently linking a targeting peptide to a therapeutic nanoparticle are known in the art.

Fluorophores

The therapeutic nanoparticles described herein can also contain at least one (e.g., two, three, or four) fluorophore covalently-linked to the therapeutic nanoparticle. In some embodiments, the fluorophore absorbs near-infrared light (e.g., Cy5.5).

A variety of different fluorophores that can be covalently linked to the therapeutic nanoparticles are known in the art. A variety of different fluorophores that can be covalently linked to the therapeutic nanoparticles are known in the art. Non-limiting examples of such fluorophores include: Sulforhodamine B, Resorufin, 3,3-Diethylthiadicarbocyanine iodide, PdTFPP, Nile Red, DY-590, DY-590, Adams Apple Red 680, Adirondack Green 520, Birch Yellow 580, Catskill Green 540, Fort Orange 600, Hemo Red, Hops Yellow, Lake Placid 490, Maple Red-Orange 620, Snake-Eye Red 900, QD525, QD565, QD585, QD605, QD655, QD705, QD800, ATTO 425, ATTO 465, ATTO 488, ATTO 495, ATTO 520, ATTO 550, ATTO 565, ATTO 590, ATTO 610, ATTO 620, ATTO 635, ATTO 647, ATTO 655, ATTO 680, ATTO 700, Alexa Fluor 633, 5-TAMRA, BOBO-3, Pro-Q Diamond, resorufin, rhod-2, Rhodamine Red-X, rhodamine, R-phycoerythrin, sulforhodamine 101, tetramethylrhodamine, Texas Red-X, X-rhod-1, Calcein red-orange, Carboxynaphthofluorescein, DiIC18(3), Alexa Fluor 546, Alexa Fluor 555, Alexa Fluor 610, Alexa Fluor 647, Alexa Fluor 680, JC-1, LOLO-1, tdTomato, mCherry, mPlum, mRaspberry, mRFP1.2, mStrawberry, mTangerine, CryptoLight CF4, CryptoLight CFS, CryptoLight CF6, R-phycoerythrin, SensiLight PBXL-3, Spectrum Orange, Spectrum Red, C3-Thiacyanine Dye, C5-Oxacyanine, nile red, MitoTracker Red CMXRos, MitoTracker Orange CMTMRos, LysoTracker Red DND-99, JC-1, Cy3.5, ReAsH-CCXXCC, AsRed2, DsRed, DsRed Dimer2, DsRed-Express T1, Fluorescein-Dibase, Magnesium Octaethylporphyrin, Magnesium Phthalocyanine, Magnesium Phthalocyanine, Merocyanine 540, Phthalocyanine, Pinacyanol-Iodide, Rose Bengal basic, Sulforhodamine 101, Tetra-t-Butylazaporphine, Zinc Octaethylporphyrin, Zinc Phthalocyanine, Lumio Red, Rhodamine 700, Styryl 8 perchlorate, Terrylen, Terrylendiimid, Thionin acetate, Dye-304, Dye-1041, Dye-4, Cresyl Violet Perchlorate, DyLight 549, 2-dodecylresorufin, 5-ROX, Alexa Fluor, Alexa Fluor 555, Alexa Fluor 594, Alexa Fluor 594, PdOEPK, PtOEPK, Amplex UltraRed, BODIPY TR-X phallacidin, BODIPY TR-X, Calcium Crimson, CellTrace BODIPY TR methyl ester, CellTracker Red CMTPX, Cy3, DiI, FluoSpheres red, LDS 751, mRFP, pHrodo, succinimidyl ester, Qdot 585, Qdot 605, QSY 7, QSY 9, Rhodamine phalloidin, Rhodamine Red-X, Tetramethylrhodamine, Texas Red, Texas Red DHPE, Lumogen Red F300 Polystyren, Lumogen Red F300 Polystyren, Platinum(II) tetraphenyltetrabenzo-porphyrin, IRDye® 800CW Phosphate, and ATTO 647N. Additional non-limiting examples of near-infrared absorbing dyes are commercially available from a variety of commercial vendors, including QCR Solutions Corp. In some embodiments of the methods described herein, the position or localization of therapeutic nanoparticle containing a covalently-linked fluorophore can be imaged in a subject (e.g., imaged in a subject following the administration of one or more doses of a therapeutic nanoparticle containing a covalently-linked fluorophore).

In some embodiments, the fluorophore is attached to the therapeutic nanoparticle through a chemical moiety that contains a secondary amine, an amide, a thioester, or a disulfide bond. Additional chemical moieties that can be used to covalently link a fluorophore to a therapeutic nanoparticle are known in the art.

A variety of different methods can be used to covalently link a fluorophore to a therapeutic nanoparticle. In some embodiments, the fluorophore is attached to the therapeutic nanoparticle through reaction of: an amino group (present in the fluorophore or on the therapeutic nanoparticle) with an active ester, carboxylate, isothiocyanate, or hydrazine (e.g., present in the fluorophore or on the therapeutic nanoparticle); through reaction of a carboxyl group (e.g., present in the fluorophore or on the therapeutic nanoparticle) in the presence of a carbiimide; through reaction of a thiol (e.g., present in the fluorophore or on the therapeutic nanoparticle) in the presence of maleimide; through the reaction of a thiol (e.g., present in the fluorophore or on the therapeutic nanoparticle) in the presence of maleimide or aceyl bromide; or through the reaction of an azide (e.g., present in the fluorophore or on the therapeutic nanoparticle) in the presence of glutaraldehyde. Additional methods for attaching a fluorophore to a therapeutic nanoparticle are known in the art.

Pharmaceutical Compositions

Also provided herein are pharmaceutical compositions that contain a therapeutic nanoparticle as described herein. Two or more (e.g., two, three, or four) of any of the types of therapeutic nanoparticles described herein can be present in a pharmaceutical composition in any combination. The pharmaceutical compositions can be formulated in any manner known in the art.

Pharmaceutical compositions are formulated to be compatible with their intended route of administration (e.g., intravenous, intraarterial, intramuscular, intradermal, subcutaneous, or intraperitoneal). The compositions can include a sterile diluent (e.g., sterile water or saline), a fixed oil, polyethylene glycol, glycerine, propylene glycol or other synthetic solvents, antibacterial or antifungal agents such as benzyl alcohol or methyl parabens, chlorobutanol, phenol, ascorbic acid, thimerosal, and the like, antioxidants such as ascorbic acid or sodium bisulfate, chelating agents such as ethylenediaminetetraacetic acid, buffers such as acetates, citrates, or phosphates, and isotonic agents such as sugars (e.g., dextrose), polyalcohols (e.g., manitol or sorbitol), or salts (e.g., sodium chloride), or any combination thereof. Liposomal suspensions can also be used as pharmaceutically acceptable carriers (see, e.g., U.S. Pat. No. 4,522,811). Preparations of the compositions can be formulated and enclosed in ampules, disposable syringes, or multiple dose vials. Where required (as in, for example, injectable formulations), proper fluidity can be maintained by, for example, the use of a coating such as lecithin, or a surfactant. Absorption of the therapeutic nanoparticles can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.). Compositions containing one or more of any of the therapeutic nanoparticles described herein can be formulated for parenteral (e.g., intravenous, intraarterial, intramuscular, intradermal, subcutaneous, or intraperitoneal) administration in dosage unit form (i.e., physically discrete units containing a predetermined quantity of active compound for ease of administration and uniformity of dosage).

Toxicity and therapeutic efficacy of compositions can be determined by standard pharmaceutical procedures in cell cultures or experimental animals (e.g., monkeys). One can, for example, determine the LD50 (the dose lethal to 50% of the population) and the ED50 (the dose therapeutically effective in 50% of the population): the therapeutic index being the ratio of LD50:ED50. Agents that exhibit high therapeutic indices are preferred. Where an agent exhibits an undesirable side effect, care should be taken to minimize potential damage (i.e., reduce unwanted side effects). Toxicity and therapeutic efficacy can be determined by other standard pharmaceutical procedures.

Data obtained from cell culture assays and animal studies can be used in formulating an appropriate dosage of any given agent for use in a subject (e.g., a human). A therapeutically effective amount of the one or more (e.g., one, two, three, or four) therapeutic nanoparticles (e.g., any of the therapeutic nanoparticles described herein) will be an amount that treats decreases cancer cell invasion or metastasis in a subject having cancer (e.g., breast cancer) in a subject (e.g., a human), treats a metastatic cancer in a lymph node in a subject, decreases or stabilizes metastatic tumor size in a lymph node in a subject, decreases the rate of metastatic tumor growth in a lymph node in a subject, decreases the severity, frequency, and/or duration of one or more symptoms of a metastatic cancer in a lymph node in a subject in a subject (e.g., a human), or decreases the number of symptoms of a metastatic cancer in a lymph node in a subject (e.g., as compared to a control subject having the same disease but not receiving treatment or a different treatment, or the same subject prior to treatment).

The effectiveness and dosing of any of the therapeutic nanoparticles described herein can be determined by a health care professional using methods known in the art, as well as by the observation of one or more symptoms of a metastatic cancer in a lymph node in a subject (e.g., a human). Certain factors may influence the dosage and timing required to effectively treat a subject (e.g., the severity of the disease or disorder, previous treatments, the general health and/or age of the subject, and the presence of other diseases).

Exemplary doses include milligram or microgram amounts of any of the therapeutic nanoparticles described herein per kilogram of the subject's weight. While these doses cover a broad range, one of ordinary skill in the art will understand that therapeutic agents, including the therapeutic nanoparticles described herein, vary in their potency, and effective amounts can be determined by methods known in the art. Typically, relatively low doses are administered at first, and the attending health care professional (in the case of therapeutic application) or a researcher (when still working at the development stage) can subsequently and gradually increase the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, and the half-life of the therapeutic nanoparticles in vivo.

The pharmaceutical compositions can be included in a container, pack, or dispenser together with instructions for administration.

Methods of Treatment

The therapeutic nanoparticles described herein were discovered to decrease cancer cell invasion and to inhibit cancer cell metastasis. In view of this discovery, provided herein are methods of decreasing cancer cell invasion or metastasis in a subject, methods of treating a metastatic cancer in a lymph node in a subject, and methods of delivering a nucleic acid to a cell present in the lymph node of a subject. Specific embodiments and various aspects of these methods are described below.

Methods of Treating Metastatic Cancer

Metastatic cancer is a cancer that originates from a cancer cell from a primary tumor that has migrated to a different tissue in the subject. In some embodiments, the cancer cell from the primary tumor can migrate to a different tissue in the subject by traveling through the blood stream or the lymphatic system of the subject. In some embodiments, the metastatic cancer is a metastatic cancer present in a lymph node in a subject.

The symptoms of metastatic cancer experienced by a subject depend on the site of metastatic tumor formation. Non-limiting symptoms of metastatic cancer in the brain of a subject include: headaches, dizziness, and blurred vision. Non-limiting symptoms of metastatic cancer in the liver of a subject include: weight loss, fever, nausea, loss of appetite, abdominal pain, fluid in the abdomen (ascites), jaundice, and swelling of the legs. Non-limiting symptoms of metastatic cancer in the bone of a subject include: pain and bone breakage following minor or no injury. Non-limiting symptoms of metastatic cancer in the lung of a subject include: non-productive cough, cough producing bloody sputum, chest pain, and shortness of breath.

A metastatic cancer can be diagnosed in a subject by a health care professional (e.g., a physician, a physician's assistant, a nurse, or a laboratory technician) using methods known in the art. For example, a metastatic cancer can be diagnosed in a subject, in part, by the observation or detection of at least one symptom of a metastatic cancer in a subject (e.g., any of those symptoms listed above). A metastatic cancer can also be diagnosed in a subject using a variety of imaging techniques (e.g., alone or in combination with the observance of one or more symptoms of a metastatic cancer in a subject). For example, the presence of a metastatic cancer (e.g., a metastatic cancer in a lymph node) can be detected in a subject using computer tomography, magnetic resonance imaging, positron emission tomography, and X-ray. A metastatic cancer (e.g., a metastatic cancer in a lymph node) can also be diagnosed by performing a biopsy of tissue from the subject (e.g., a biopsy of a lymph node from the subject).

A metastatic tumor can form in a variety of different tissues in a subject, including, but not limited to: brain, lung, liver, bone, peritoneum, adrenal gland, skin, and muscle. The primary tumor can be of any cancer type, including but not limited to: breast, colon, kidney, lung, skin, ovarian, pancreatic, rectal, stomach, thyroid, or uterine cancer.

Any one or more of the therapeutic nanoparticles described herein can be administered to a subject having a metastatic cancer. The one or more therapeutic nanoparticles can be administered to a subject in a health care facility (e.g., in a hospital or a clinic) or in an assisted care facility. In some embodiments, the subject has been previously diagnosed as having a cancer (e.g., a primary cancer). In some embodiments, the subject has been previously diagnosed as having a metastatic cancer (e.g., a metastatic cancer in the lymph node). In some embodiments, the subject has already received therapeutic treatment for the primary cancer. In some embodiments, the primary tumor of the subject has been surgically removed prior to treatment with one of the therapeutic nanoparticles described herein. In some embodiments, at least one lymph node has been removed from the subject prior to treatment with one of the therapeutic nanoparticles described herein. In some embodiments, the subject may be in a period of cancer remission.

In some embodiments, the administering of at least one therapeutic nanoparticle results in a decrease (e.g., a significant or observable decrease) in the size of a metastatic tumor present in a lymph node, a stabilization of the size (e.g., no significant or observable change in size) of a metastatic tumor present in a lymph node, or a decrease (e.g., a detectable or observable decrease) in the rate of the growth of a metastatic tumor present in a lymph node in a subject. A health care professional can monitor the size and/or changes in the size of a metastatic tumor present in a lymph node in a subject using a variety of different imaging techniques, including but not limited to: computer tomography, magnetic resonance imaging, positron emission tomography, and X-ray. For example, the size of a metastatic tumor present in a lymph node of a subject can be determined before and after therapy in order to determine whether there has been a decrease or stabilization in the size of the metastatic tumor in the subject in response to therapy. The rate of growth of a metastatic tumor in the lymph node of a subject can be compared to the rate of growth of a metastatic tumor in another subject or population of subjects not receiving treatment or receiving a different treatment. A decrease in the rate of growth of a metastatic tumor in the lymph node of a subject can also be determined by comparing the rate of growth of a metastatic tumor in a lymph node both prior to and following a therapeutic treatment (e.g., treatment with any of the therapeutic nanoparticles described herein). In some embodiments, the visualization of a metastatic tumor (e.g., a metastatic tumor in a lymph node) can be performed using imaging techniques that utilize a labeled probe or molecule that binds specifically to the cancer cells in the metastatic tumor (e.g., a labeled antibody that selectively binds to an epitope present on the surface of the primary cancer cell).

In some embodiments, the administering of at least one therapeutic nanoparticle to the subject results in a decrease in the risk of developing an additional metastatic tumor in a subject already having at least one metastatic tumor (e.g., a subject already having a metastatic tumor in a lymph node) (e.g., as compared to the rate of developing an additional metastatic tumor in a subject already having a similar metastatic tumor but not receiving treatment or receiving an alternative treatment). A decrease in the risk of developing an additional metastatic tumor in a subject already having at least one metastatic tumor can also be compared to the risk of developing an additional metastatic tumor in a population of subjects receiving no therapy or an alternative form of cancer therapy.

In some embodiments, administering a therapeutic nanoparticle to the subject decreases the risk of developing a metastatic cancer (e.g., a metastatic cancer in a lymph node) in a subject having (e.g., diagnosed as having) a primary cancer (e.g., a primary breast cancer) (e.g., as compared to the rate of developing a metastatic cancer in a subject having a similar primary cancer but not receiving treatment or receiving an alternative treatment). A decrease in the risk of developing a metastatic tumor in a subject having a primary cancer can also be compared to the rate of metastatic cancer formation in a population of subjects receiving no therapy or an alternative form of cancer therapy.

A health care professional can also assess the effectiveness of therapeutic treatment of a metastatic cancer (e.g., a metastatic cancer in a lymph node of a subject) by observing a decrease in the number of symptoms of metastatic cancer in the subject or by observing a decrease in the severity, frequency, and/or duration of one or more symptoms of a metastatic cancer in a subject. A variety of symptoms of a metastatic cancer are known in the art and are described herein. Non-limiting examples of symptoms of metastatic cancer in a lymph node include: pain in a lymph node, swelling in a lymph node, appetite loss, and weight loss.

In some embodiments, the administering can result in an increase (e.g., a significant increase) the chance of survival of a primary cancer or a metastatic cancer in a subject (e.g., as compared to a population of subjects having a similar primary cancer or a similar metastatic cancer but receiving a different therapeutic treatment or no therapeutic treatment). In some embodiments, the administering can result in an improved prognosis for a subject having a primary cancer or a metastatic cancer (e.g., as compared to a population of subjects having a similar primary cancer or a similar metastatic cancer but receiving a different therapeutic treatment or no therapeutic treatment).

Methods of Decreasing Cancer Cell Invasion or Metastasis

Also provided are methods of decreasing (e.g., a significant or observable decrease) cancer cell invasion or metastasis in a subject that include administering at least one therapeutic nanoparticle described herein to the subject in an amount sufficient to decrease cancer cell invasion or metastasis in a subject.

In some embodiments of these methods, the cancer cell metastasis is from a primary tumor (e.g., any of the primary tumors described herein) to a secondary tissue (e.g., a lymph node) in a subject. In some embodiments of these methods, the cancer cell metastasis is from a lymph node to a secondary tissue (e.g., any of the secondary tissues described herein) in the subject.

In some embodiments, the cancer cell invasion is the migration of a cancer cell into a tissue proximal to the primary tumor. In some embodiments, the cancer cell invasion is the migration of a cancer cell from a primary tumor into the lymphatic system. In some embodiments, the cancer cell invasion is the migration of a metastatic cancer cell present in the lymph node into the lymphatic system or the migration of a metastatic cancer cell present in a secondary tissue to an adjacent tissue in the subject.

Cancer cell invasion in a subject can be assessed or monitored by visualization using any of the imaging techniques described herein. For example, one or more tissues of a subject having a cancer or metastatic cancer can be visualized at two or more time points (e.g., at a time point shortly after diagnosis with a cancer and at later time point). In some embodiments, a decrease in cancer cell invasion in a subject can be detected by observing a decrease in the spread of a primary tumor through a specific tissue in the subject (when the spread of the primary tumor is assessed through the imaging techniques known in the art or described herein). In some embodiments, a decrease in cancer cell invasion can be detected by a reduction in the number of circulating primary cancer cells or circulating metastatic cancer cells in the blood or lymph of a subject.

Cancer cell metastasis can be detected using any of the methods described herein or known in the art. For example, successful reduction of cancer cell metastasis can be observed as a decrease in the rate of development of an additional metastatic tumor in a subject already having at least one metastatic tumor (e.g., a subject already having a metastatic tumor in a lymph node) (e.g., as compared to the rate of development of an additional metastatic tumor in a subject or a population of subjects already having a similar metastatic tumor but not receiving treatment or receiving an alternative treatment). Successful reduction of cancer cell metastasis can also be observed as a decrease in the risk of developing at least one metastatic cancer (e.g., a metastatic cancer in a lymph node) in a subject having (e.g., diagnosed as having) a primary cancer (e.g., a primary breast cancer) (e.g., as compared to the risk of developing a metastatic cancer in a subject or a population of subjects having a similar primary cancer but not receiving treatment or receiving an alternative treatment).

Dosing, Administration, and Compositions

In any of the methods described herein, the therapeutic nanoparticle can be administered by a health care professional (e.g., a physician, a physician's assistant, a nurse, or a laboratory or clinic worker), the subject (i.e., self-administration), or a friend or family member of the subject. The administering can be performed in a clinical setting (e.g., at a clinic or a hospital), in an assisted living facility, or at a pharmacy.

In some embodiments of any of the methods described herein, the therapeutic nanoparticle is administered to a subject that has been diagnosed as having a cancer (e.g., having a primary cancer or a metastatic cancer). In some embodiments, the subject has been diagnosed with breast cancer (e.g., a metastatic breast cancer). In some non-limiting embodiments, the subject is a man or a woman, an adult, an adolescent, or a child. The subject can have experienced one or more symptoms of a cancer or metastatic cancer (e.g., a metastatic cancer in a lymph node). The subject can also be diagnosed as having a severe or an advanced stage of cancer (e.g., a primary or metastatic cancer). In some embodiments, the subject may have been identified as having a metastatic tumor present in at least one lymph node. In some embodiments, the subject may have already undergone lymphectomy and/or mastectomy.

In some embodiments of any of the methods described herein, the subject is administered at least one (e.g., at least 2, 3, 4, 5, 6, 7, 8, 9, 10, 15, 20, 25, or 30) dose of a composition containing at least one (e.g., one, two, three, or four) of any of the magnetic particles or pharmaceutical compositions described herein. In any of the methods described herein, the at least one magnetic particle or pharmaceutical composition (e.g., any of the magnetic particles or pharmaceutical compositions described herein) can be administered intravenously, intaarterially, subcutaneously, intraperitoneally, or intramuscularly to the subject. In some embodiments, the at least magnetic particle or pharmaceutical composition is directly administered (injected) into a lymph node in a subject.

In some embodiments, the subject is administered at least one therapeutic nanoparticle or pharmaceutical composition (e.g., any of the therapeutic nanoparticles or pharmaceutical compositions described herein) and at least one additional therapeutic agent. The at least one additional therapeutic agent can be a chemotherapeutic agent (e.g., cyclophosphamide, mechlorethamine, chlorambucil, melphalan, daunorubicin, doxorubicin, epirubicin, idarubicin, mitoxantrone, valrubicin, paclitaxel, docetaxel, etoposide, teniposide, tafluposide, azacitidine, azathioprine, capecitabine, cytarabine, doxifluridine, fluorouracil, gemcitabine, mercaptopurine, methotrexate, tioguanine, bleomycin, carboplatin, cisplatin, oxaliplatin, bortezomib, carfilzomib, salinosporamide A, all-trans retinoic acid, vinblastine, vincristine, vindesine, and vinorelbine) and/or an analgesic (e.g., acetaminophen, diclofenac, diflunisal, etodolac, fenoprofen, flurbiprofen, ibuprofen, indomethacin, ketoprofen, ketorolac, meclofenamate, mefenamic acid, meloxicam, nabumetone, naproxen, oxaprozin, phenylbutazone, piroxicam, sulindac, tolmetin, celecoxib, buprenorphine, butorphanol, codeine, hydrocodone, hydromorphone, levorphanol, meperidine, methadone, morphine, nalbuphine, oxycodone, oxymorphone, pentazocine, propoxyphene, and tramadol).

In some embodiments, at least one additional therapeutic agent and at least one therapeutic nanoparticle (e.g., any of the therapeutic nanoparticles described herein) are administered in the same composition (e.g., the same pharmaceutical composition). In some embodiments, the at least one additional therapeutic agent and the at least one therapeutic nanoparticle are administered to the subject using different routes of administration (e.g., at least one additional therapeutic agent delivered by oral administration and at least one therapeutic nanoparticle delivered by intravenous administration).

In any of the methods described herein, the at least one therapeutic nanoparticle or pharmaceutical composition (e.g., any of the therapeutic nanoparticles or pharmaceutical compositions described herein) and, optionally, at least one additional therapeutic agent can be administered to the subject at least once a week (e.g., once a week, twice a week, three times a week, four times a week, once a day, twice a day, or three times a day). In some embodiments, at least two different therapeutic nanoparticles are administered in the same composition (e.g., a liquid composition). In some embodiments, at least one therapeutic nanoparticle and at least one additional therapeutic agent are administered in the same composition (e.g., a liquid composition). In some embodiments, the at least one therapeutic nanoparticle and the at least one additional therapeutic agent are administered in two different compositions (e.g., a liquid composition containing at least one therapeutic nanoparticle and a solid oral composition containing at least one additional therapeutic agent). In some embodiments, the at least one additional therapeutic agent is administered as a pill, tablet, or capsule. In some embodiments, the at least one additional therapeutic agent is administered in a sustained-release oral formulation. In some embodiments, the one or more additional therapeutic agents can be administered to the subject prior to administering the at least one therapeutic nanoparticle or pharmaceutical composition (e.g., any of the therapeutic nanoparticles or pharmaceutical compositions described herein). In some embodiments, the one or more additional therapeutic agents can be administered to the subject after administering the at least one therapeutic nanoparticle or pharmaceutical composition (e.g., any of the magnetic particles or pharmaceutical compositions described herein). In some embodiments, the one or more additional therapeutic agents and the at least one therapeutic nanoparticle or pharmaceutical composition (e.g., any of the therapeutic nanoparticles or pharmaceutical compositions described herein) are administered to the subject such that there is an overlap in the bioactive period of the one or more additional therapeutic agents and the at least one therapeutic nanoparticle (e.g., any of the therapeutic nanoparticles described herein) in the subject.

In some embodiments, the subject can be administered the at least one therapeutic nanoparticle or pharmaceutical composition (e.g., any of the therapeutic nanoparticles or pharmaceutical compositions described herein) over an extended period of time (e.g., over a period of at least 1 week, 2 weeks, 3 weeks, 1 month, 2 months, 3 months, 4 months, 5 months, 6 months, 7 months, 8 months, 9 months, 10 months, 11 months, 12 months, 1 year, 2 years, 3 years, 4 years, 5 years, or 10 years). A skilled medical professional may determine the length of the treatment period using any of the methods described herein for diagnosing or following the effectiveness of treatment (e.g., using the methods above and those known in the art). As described herein, a skilled medical professional can also change the identity and number (e.g., increase or decrease) of therapeutic nanoparticles (and/or one or more additional therapeutic agents) administered to the subject and can also adjust (e.g., increase or decrease) the dosage or frequency of administration of at least one therapeutic nanoparticle (and/or one or more additional therapeutic agents) to the subject based on an assessment of the effectiveness of the treatment (e.g., using any of the methods described herein and known in the art). A skilled medical professional can further determine when to discontinue treatment (e.g., for example, when the subject's symptoms are significantly decreased).

EXAMPLES

The invention is further described in the following examples, which do not limit the scope of the invention described in the claims.

Example 1. Uptake and Activity of Therapeutic Nanoparticles in Breast Tumor Cells Twenty to thirty-five nm dextran-coated therapeutic magnetic nanoparticles were conjugated to the tumor-targeting peptide, cRGD. These therapeutic magnetic nanoparticles were further functionalized with knock-down locked nucleic acid (LNA) oligonucleotides (1.5 nmoles LNA/mL) targeting human miRNA-10b and the fluorophore, Cy5.5. The resulting therapeutic magnetic nanoparticles are hereafter referred to as "MN-RGD-anti-miR-10b" (see, FIG. 1). These therapeutic magnetic nanoparticles were generated as described below.

Synthesis of Therapeutic Magnetic Nanoparticles

Therapeutic magnetic nanoparticle (MN) synthesis was modified from a protocol published previously (Medarova et al., *Nat. Protocols* 1:429-435, 2006). Briefly, 9 g of Dextan-T10 (Pharmacosmos, Denmark) was dissolved in 30 mL of double-distilled water and stirred in a round bottom flask on ice. Iron (III) chloride hexahydrate ($FeCl_3 \cdot 6H_2O$) (0.65 g) was added while flushing Argon gas into the reaction mixture for an hour. Iron (II) chloride tetrahydrate ($FeCl_2 \cdot 4H_2O$) (0.4 g) was added into the mixture, and then 15 mL of concentrated cold $NH_4OH$ (~28%) was added dropwise to the stirring mixture. The temperature increased to 85° C. for an hour to induce the formation of a nanoparticulate colloidal mixture, cooled to room temperature, and concentrated to 20 mL using Amicon Ultra centrifugal units (molecular weight cut-off of 30 kDa; Millipore). The resulting 20 mL dextran-coated therapeutic magnetic nanoparticles were cross-linked and aminated by the subsequent addition of 35 mL of 5 M NaOH, 14 mL of concentrated epichlorohydrin (8 hours) and 60 mL of concentrated $NH_4OH$. The nanoparticle solution was purified using a dialysis bag (molecular weight cut-off of 14 kDa) against water and 20 mM citrate buffer (pH 8.0), and then concentrated to 20 mL by Amicon Ultra centrifugal units. The nanoparticle concentration was determined based on iron concentration (10.8 mg/mL Fe) and measured spectrophotometrically, as described in Kumar et al. (*Cancer Res.* 70:7553-7561, 2010). The size of the nanoparticles was determined by dynamic light scattering using Zetasizer Nano ZS (Malvern Instruments Ltd) and nanoparticles of 23.5±3.5 nm were selected as suitable for accumulation in tumors and lymph nodes. The number of amine groups was found to be 73 per nanoparticle.

One milligram of the near-infrared dye Cy5.5 monoreactive NHS ester (GE Healthcare) was dissolved in 100 µL of anhydrous DMSO and incubated with MN (10 mg Fe) in 20 mM citrate buffer (pH 8.0) overnight. The nanoparticles were purified using Sephadex PD-10 column (GE Healthcare) against PBS. The number of Cy5.5 molecules per nanoparticle was quantified spectrophotmometrically, and found to be four Cy5.5 molecules per MN. The nanoparticles were further conjugated to heterofunctional linker N-succinimidyl 3-[2-pyridyldithio]-propionate (SPDP) (Pierce Biotechnology) in order to provide a thiol reactive terminus for LNA and cRGD conjugation. Briefly, 10 mg SPDP was dissolved in 500 µL anhydrous dimethyl sulfoxide (DMSO) and incubated with Cy5.5-labeled MN.

The MN were further conjugated to cRGD peptide through its cysteine terminus in PBS and purified with a Sephadex PD-10 column. The LNA oligonucleotides were then conjugated to MN. Briefly, the thiolated 5' terminus of the oligonucleotide was activated via 3% TCEP-treatment in nuclease-free PBS. The LNA oligonucleotides were purified using ammonium acetate/ethanol precipitation method. After Tris(2-carboxyethyl)phosphine hydrochloride (TCEP)-activation and purification, the oligonucleotides were resuspended in PBS and 50 mM ethylenediaminetetraacetic acid (EDTA), and incubated with the nanoparticles overnight. The resulting probe was purified using a G-50 Sephadex disposable quick spin columns (Roche Applied Science). The quantification of cRGD and LNA per MN was performed as described previously (Kumar et al., *Cancer Res.* 70:7553-7561, 2010) and determined as fifteen cRGD per MN and ten LNA per MN.

Locked Nucleic Acids

The short locked nucleic acid (LNA) oligonucleotide sequence (anti-miR10b), 5'-ThioMC6-D/CACAAATTCG-GTTCTACAGGGTA-3' (SEQ ID NO: 18), directed against miRNA-10b, and a mismatch scrambled sequence (scr-miR), 5'-Thio MC6-D/GTGTAACACGTCTATACGCCCA-3' (SEQ ID NO: 17), were synthesized by Exiqon Inc. A 5'-thiol modification was inserted into both sequences for conjugation to therapeutic magnetic nanoparticles and a 3'-Cy3 modification was inserted in the sequences for in vitro studies. The thiol modifications on the oligonucleotides were activated with treatment of 3% Tris(2-carboxyethyl) phosphine hydrochloride, followed by purification with ammonium acetate/ethanol precipitation, prior to conjugation to the nanoparticles as described in Medarova et al. (*Nat. Med.* 13:372-377, 2007) and Kumar et al. (*Cancer Res.* 70:7553-7561, 2010).

Synthesis of cRGD Peptide

The synthesis of Cyclic RGDfK-PEG-Cys-(Boc) was performed as follows. Cyclo Arg-Gly-Asp-D-Phe-Lys(PEG-PEG) (where PEG=8-amino-3,6-dioxaoctanoic acid) (13.41 mg, 0.015 mmol, Peptide International Inc.) was added to a solution of Boc-Cys(Tris)-Osu (11.2 mg, 0.02 mmol) in dimethylformamide (1 mL). The reaction mixture pH (pH 8.5 to 9) was maintained using diisopropyl ethylmine, and the resulting reaction mixture was allowed to stir at room temperature overnight. The product of the reaction was confirmed by thin layer chromatography, and isolated using the high pressure liquid chromatography (HPLC) gradient method. The collected fractions were lyophilized and obtained as a white powder. The final product was analyzed by MALDI-TOF mass spectrometry.

Cyclic RGDfK-PEG-Cys-(Boc) was treated with 2-3 mL of anhydrous trifluoroacetic acid at room temperature for 30 minutes. The resulting volatile mixture was completely removed under vacuum. Afterwards, the residue was dissolved in 100 mM $NH_4OAc$ buffer (3 mL). The resulting solution was filtered, and the filtrate was purified by HPLC. The final product was analyzed by MALDI-TOF mass spectrometry.

Experiments were performed to determine whether MN-RGD-anti-miR-10b would be taken up by human breast cancer cells. In these experiments, human breast cancer cells (MDA-MB-231 (gfp) cells) were incubated with MN-RGD-anti-miR-10b for 48 hours, and the data gathered using flow cytometry (for Cy5.5) and confocal microscopy (for Cy5.5 and LNA). The details of the materials and methods used in these experiments are described below.

Cell Lines

Human stably-transfected MDA-MB-231-luc-D3H2LN metastatic breast cancer cell lines were authenticated based on viability, recovery, growth, morphology, and isoenzymology by the supplier (Caliper Life Sciences). The cells were passaged as recommended by the supplier.

Fluorescence Confocal Microscopy

Fluorescence confocal microscopy was performed on MDA-MB-231-GFP breast cancer cells. The cells ($2 \times 10^6$) were incubated with MN-anti-miR10b or MN-scr-miR (45 µg Fe, 4 nmols LNA) for 48 hours at 37° C. on a cover slip in an 8-well plate. The cells were then washed three times with Hank's buffered salt solution (HBSS) and fixed with 2% formaldehyde for 10 minutes. The cells were then washed three times with Dulbecco's PBS (DPBS), and the cover slip placed on a glass slide with Vectashield mounting medium (Vector Laboratories). The slides were dried in a hood for 30 minutes in a dark room. The cells were imaged by confocal microscopy in the fluorescein isothiocyanate (FITC) channel (GFP detection), the Cy3 channel (LNA detection), and the Cy5.5 channel (MN detection) using a Zeiss LSM 5 Pascal laser confocal microscope. The Zeiss RGB vario laser module consists of an argon laser (458/488/514 nm) and two helium-neon lasers (543 and 633 nm). Image acquisition and analyses were performed using Zeiss LSM 5 Pascal Confocal Microscopy Software (Release 3.2).

Flow Cytometry

MN-anti-miR10b and MN-scr-miR uptake by MDA-MB-231-GFP cells and 4T1 was analyzed by flow cytometry. MDA-MB-231-GFP cells were incubated with the probes (45 µg Fe, 4 nmols LNA) for 48 hours and 4T1 cells were incubated with the probes (45 mg Fe, 4 nmol LNA) for 24 hours at 37° C. in an 8-well plate, washed twice with HBBS buffer, and removed from the plate using Hank's based enzyme-free cell dissociation buffer. The cells were then fixed in 2% paraformaldehyde for 1 hour at 4° C. and diluted in sheath solution for flow cytometry measurements. Nanodrug uptake was analyzed in the FL4 channel (Cy5.5, MN) and FL2 channel (Cy3, LNA oligonucleotides) using FACSCalibur (Becton Dickinson) equipped with the CellQuest software package.

Figure 2:
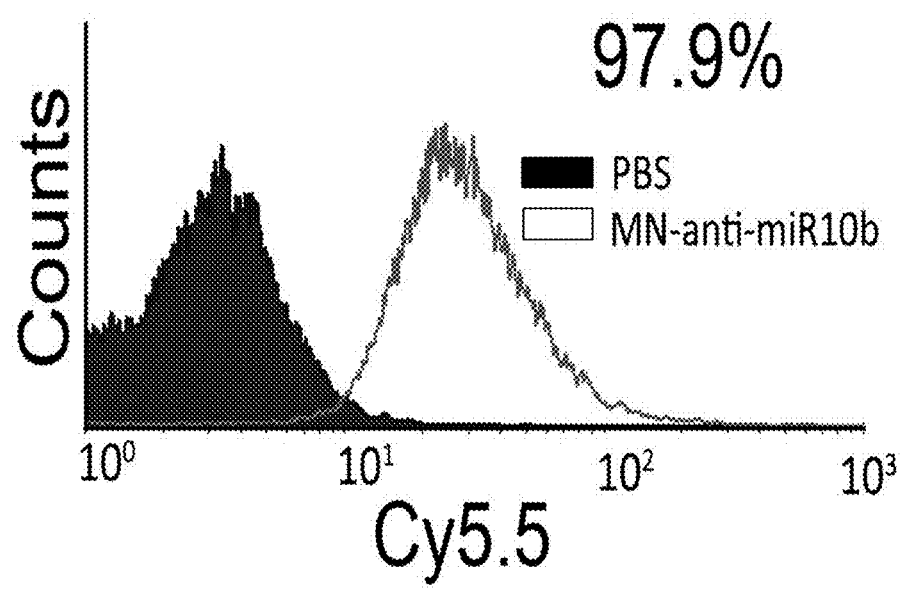
FIG. 2 is a graph of flow cytometry data of MDA-MB-231 human breast cancer cells following a 48-hour incubation with MN-RGD-anti-miR-10b.
Figure 16:
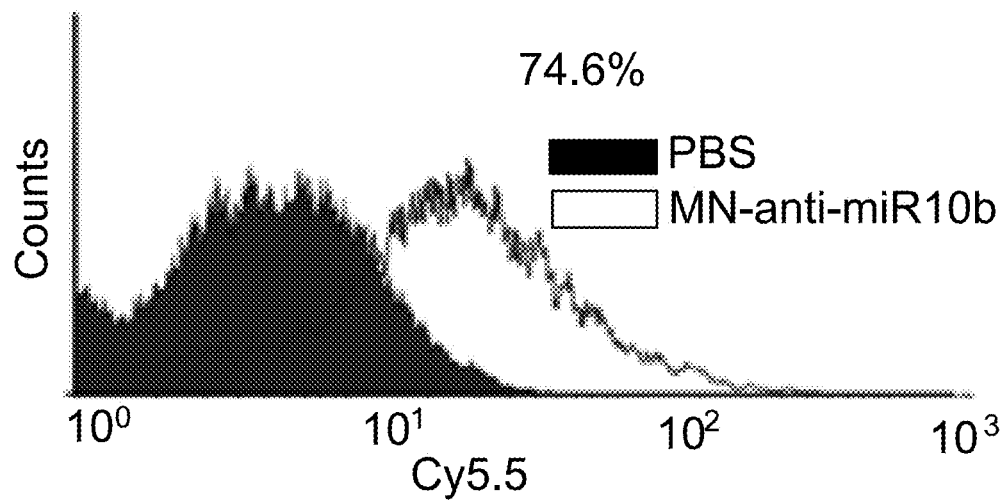
FIG. 16 is a graph of flow cytometry data of 4T1 mouse metastatic breast cancer cells following a 24-hour incubation with MN-RGD-anti-miR-10b.

The resulting data from these experiments show that 97.9% of the MDA-MB-231 cells took up MN-RGD-anti-miR-10b following 48 hours of incubation (FIG. 2). Confocal microscopy of MDA-MB-231(gfp) cells also showed staining for both Cy5.5 (blue) and LNA(red) following 48-hour incubation with MN-RGD-anti-miR-10b, further indicating the uptake of MN-RGD-anti-miR-10b by these cells. The resulting data also show that 74.6% of the 4T1 cells took up MN-RGD-anti-miR-10b following 24 hours of incubation (FIG. 16).

Quantitative RT-PCR was performed to determine whether uptake of MN-RGD-anti-miR-10b by the MDA-MB-231(gfp) cells results in a decrease in miR-10b levels in the cells. These experiments were performed as described below.

Real-Time Quantitative Reverse Transcription-PCR

To measure the extent of miR-10b knockdown by the nanodrug, MDA-MB-231 cells and 4T1 cells were incubated with MN-anti-miR10b and MN-scr-miR (45 µg 4 nmols LNA) for 48 hours at 37° C. The miRNA enriched fraction from total extracted RNA was harvested using the miRNeasy mini kit, according to the manufacturer's protocol (Qiagen, Inc.). The relative levels of miR-10b were determined by real-time quantitative reverse transcription-PCR (qRT-PCR; Taqman protocol) and compared to the internal housekeeping gene SNORD44. Taqman analysis was carried out using an ABI Prism 7700 sequence detection system (PE Applied Biosystems). The primers were provided by the manufacturer (RT2 miRNA First Strand Kit; SABiosciences).

Figure 3:
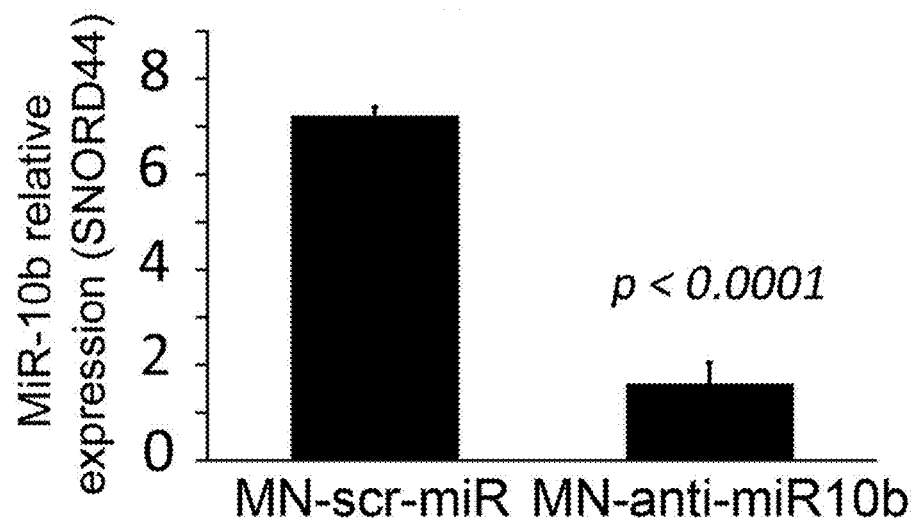
FIG. 3 is a graph showing the levels of miR-10b expression determined by quantitative reverse transcriptase polymerase chain reaction (qRT-PCR) in MDA-MB-231 human breast cancer cells following a 48-hour incubation with MN-RGD-anti-miR-10b or a corresponding magnetic nanoparticle (MN-scr-miR) containing a scrambled nucleic acid rather than the anti-miR10b nucleic acid. The data shown are represented as mean±standard deviation (p<0.0001, n=3).
Figures 4A, 4C, 4E:
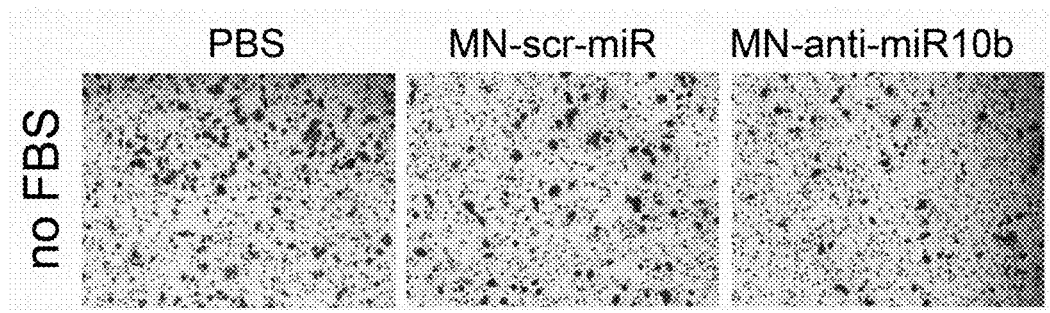
FIGS. 4A-F are a set of six photomicrographs showing the migration of MDA-MB-231 cells following treatment with MN-RGD-anti-miR-10b (4E and 4F), control magnetic particles (MN-scr-miR; 4C and 4D), or phosphate buffered saline (PBS)(4A and 4B) in the presence or absence of 10% FBS.
Figures 4B, 4D, 4F:
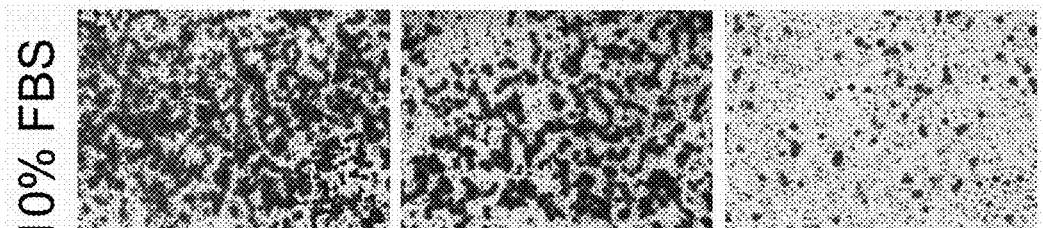
Figures 5A, 5C, 5E:
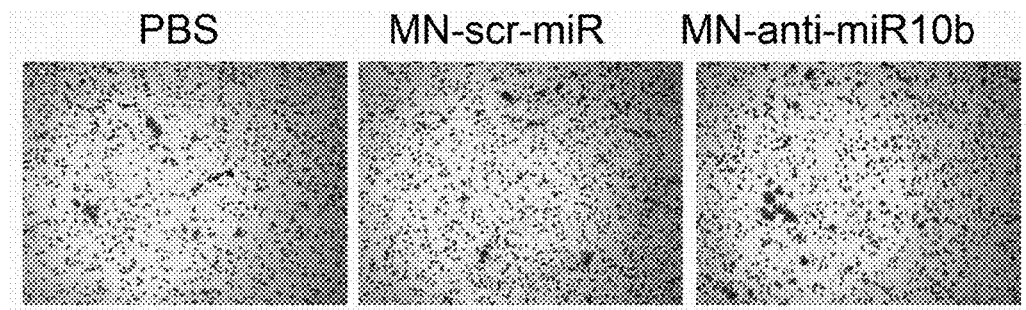
FIGS. 5A-F is a set of six photomicrographs showing the invasion of MDA-MB-231 cells following treatment with MN-RGD-anti-miR-10b (5E and 5F), control magnetic particles (MN-scr-miR; 5C and 5D), or PBS (5A and 5B) in the presence or absence of 10% FBS.
Figures 5B, 5D, 5F:
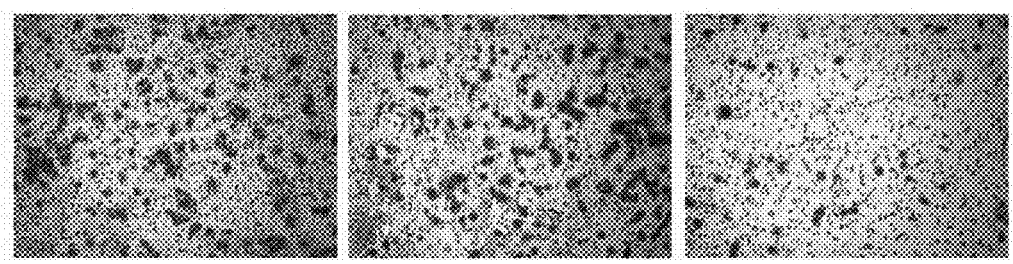
Figure 17:
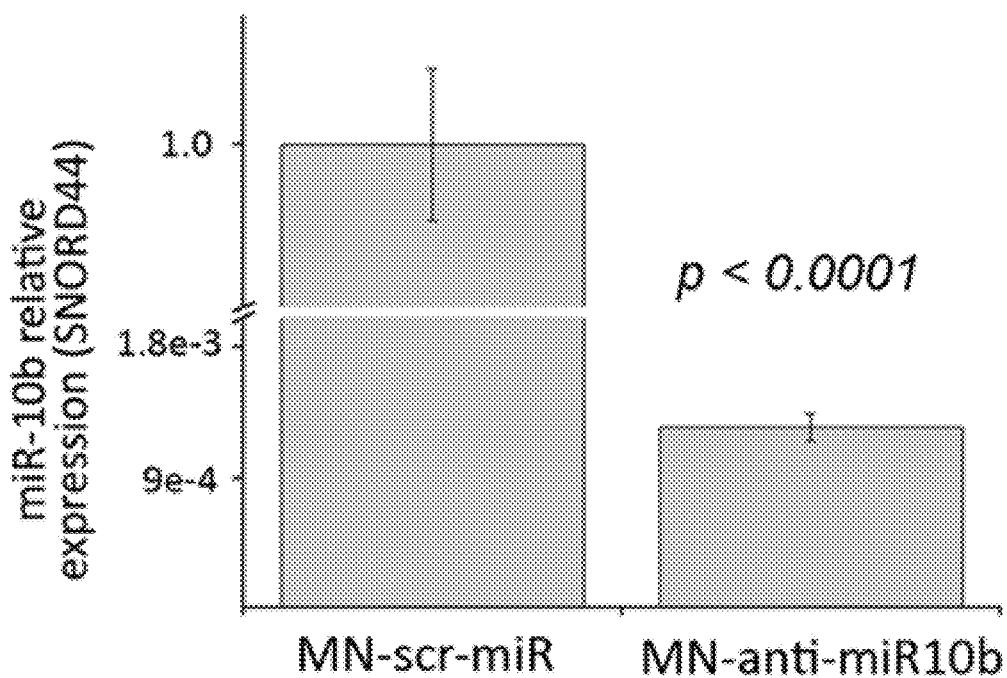
FIG. 17 a graph showing levels of miR-10b expression determined by quantitative reverse transcriptase polymerase chain reaction (qRT-PCR) in 4T1 mouse metastatic breast cancer cells following a 24-hour incubation with MN-RGD-anti-miR-10b or a corresponding magnetic nanoparticle (MN-scr-miR) containing a scrambled nucleic acid rather than the anti-miR10b nucleic acid. The data shown are represented as mean±standard deviation ($p \leq 0.0001$, n=3).

The data from these experiments show that MDA-MB-231(gfp) cells treated with MN-RGD-anti-miR-10b for 48 hours have a 87.8±6.2% decrease in miR-10b levels compared to MDA-MB-231(gfp) cells treated for 48 hours with a corresponding magnetic nanoparticle containing a scrambled nucleic acid rather than the anti-miR-10b nucleic acid (FIG. 3). These data indicate that a ~88% downregulation in miR-10b expression can be achieved by the administration of just 1.5 nmol/mL of LNA, when delivered using MN-RGD-anti-miR-10b. The data from these experiments also show that MN-RGD-anti-miR-10b mediated a knockdown of the miR-10b expression in 4T1 cells treated with MN-RGD-anti-miR-10b for 24 hours compared to 4T1 cells treated for 24 hours with a corresponding magnetic nanoparticle containing a scrambled nucleic acid rather than the anti-miR-10b nucleic acid (FIG. 17). Thus, the therapeutic nanoparticles described herein provide an efficient means for downregulating a target nucleic acid (e.g., an miRNA involved in cancer cell invasion or metastasis, or an anti-apoptotic mRNA) in a target cancer cell.

Additional experiments were performed in order to assess the toxicity of MN-RGD-anti-miR-10b in MDA-MB-231 (gfp) cells. In these experiments, MDA-MB-231(gfp) cells were treated with either MN-RGD-anti-miR-10b or control magnetic nanoparticles (magnetic nanoparticles having anti-miR-10b and no RGD; magnetic nanoparticles having control LNA-scrambled nucleic acid and RGD; magnetic nanoparticles having control LNA-scrambled nucleic acid and no RGD) and apoptosis determined using a deoxynucleotidyl transferase dUTP nick end-labeling (TUNEL) assay. The resulting data show that treatment with MN-RGD-anti-miR-10b does not induce apoptotic cell death in MDA-MB-231 (gfp) cells. These data indicate a lack of MN-RGD-anti-miR-10b cytotoxicity.

Example 2. Therapeutic Nanoparticles Decrease Breast Tumor Cell Invasion and Migration Additional experiments were performed to determine whether treatment of breast tumor cells with MN-RGD-anti-miR-10b would result in a decrease in tumor cell invasion and/or migration. In these experiments, MDA-MB-231(gfp) cells were treated with MN-RGD-anti-miR-10b or a control magnetic nanoparticle containing a scrambled oligonucleotide (MN-scr-miR) for 48 hours and then analyzed using standard cell invasion and migration kits (Cell Biolabs, Inc., San Diego, Calif.). These experiments were performed according to the supplier's instructions. Briefly, MDA-MB-231 (0.1×106) cells were plated in each insert containing membrane (pore size 8 µm) and corresponding nanodrug (60 µg, 5.0 nmol LNA) was added with/without 10% FCS (fetal calf serum), and incubated for 24 hours for the migration assay and 48 hours for the invasion assay. The inserts were stained with the supplier's kit and membranes are imaged by light microscopy to score migration and invasion.

The resulting data show that migration and invasion stimulated by 10% FBS were both abrogated by MN-RGD-anti-miR-10b and not the control magnetic nanoparticles (MN-scr-miR) (see, FIGS. 4A-F and 5A-F). These data indicate that administration of MN-RGD-anti-miR-10b to subjects could have a significant impact on metastatic outcome in subjects having a cancer.

Example 3. Therapeutic Nanoparticle Delivery to a Mouse Breast Cancer Model

Additional experiments were performed in nude mice implanted orthotopically with the MDA-MB-231(luc) cell line to determine whether the therapeutic nanoparticles described herein would show significant lymphotropism when injected intravenously into tumor-bearing mice, and to determine whether the therapeutic nanoparticles described herein can be used to treat primary and metastatic tumors in vivo. In vivo magnetic resonance imagine (MM) was used to obtain information about the time course of magnetic particle delivery to tumor cells (Kumar et al., Cancer Res. 7553-7561, 2010; Medarova et al., Cancer Res. 69:1182-1189, 2009). These experiments were performed using the methods described below.

Animal Models

Six-week old female nude mice (nu/nu or NIH III nude) were implanted orthotopically with the human breast adenocarcinoma MDA-MB-231-luc-D3H2LN cell line (Caliper Life Sciences, Hopkinton, Mass.). In this model, orthotopically-implanted tumors progress from localized disease to lymph node metastasis. The tumor cells are transformed with luciferase and can be detected by noninvasive bioluminescence imaging for correlative analysis of tumor burden.

In Vivo Magnetic Resonance Imaging (MRI)

MRI was performed before and 24-hours after intravenous administration of the therapeutic magnetic nanoparticles using a 9.4T Bruker horizontal bore scanner with ParaVision 5.1 software. The imaging protocol consisted of coronal T2-weighted spin echo (SE) pulse sequences with the following parameters: SE repetition time/echo time (TE)=2000/[8, 16, 24, 32, 40, 48, 56, 64]; field of view (FOV)=32×34 mm$^2$; matrix size=128×128 pixels; slice thickness=0.5 mm; in plane resolution=250×250 µm$^2$. Images were reconstructed and analyzed by Marevisi 3.5 software (Institute for Biodiagnostics, National Research Council, Canada). T2 maps were constructed according to established protocol by fitting T2 readings for each of the eight TEs to a standard exponential decay curve.

T2 relaxation times were calculated by manually segmenting out the tumor on MR images from each slice for every animal before and after nanodrug injection. Longitudinal relaxation rate (R2=1/T2) was determined for each slice and ΔR2 was calculated by subtracting the R2 readings before from those after nanodrug administration.

Figures 6A, 6B:
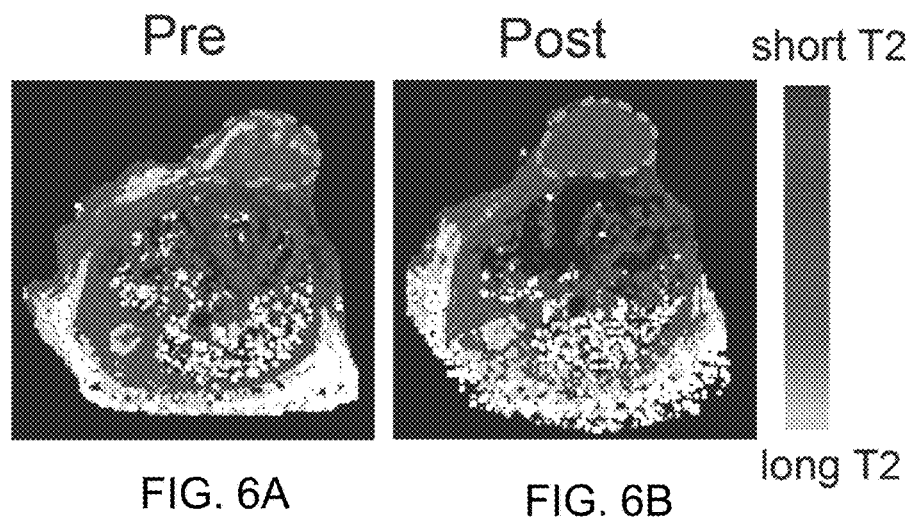
FIGS. 6A and 6B are two T2 weighted magnetic resonance images showing the MN-anti-miR10b accumulation in orthotopic MDA-MB-231-luc-D3H2LN tumors before (6A) and 24-hours after (6B) MN-anti-miR10b injection. Short T2 relaxation times are shown using darker shading, while longer T2 relaxation times are shown in lighter shading.
Figure 7:
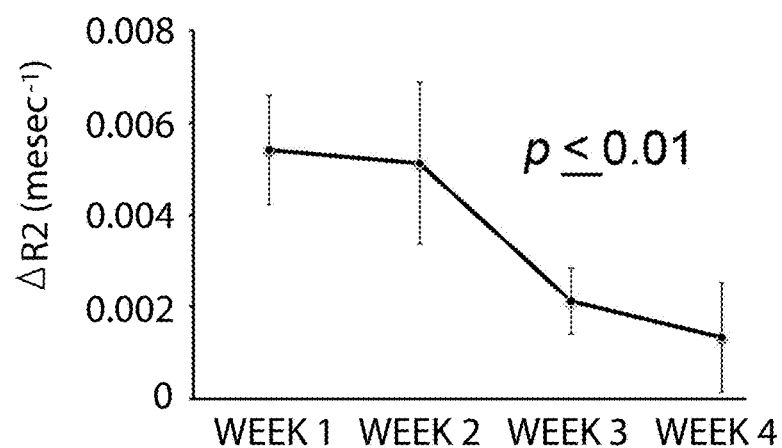
FIG. 7 is a graph showing the difference in T2 relaxation times (ΔR2) in $msec^{-1}$ of orthotopic MDA-MB-231-D3H2LN tumors before or after MN-anti-miR10b injection (1/T2 pre-injection–1/T2 post-injection, ms). The data shown are the mean±standard deviation ($p \leq 0.01$, n=6).

The data from these experiments show that the therapeutic magnetic nanoparticles are successfully delivered to the tumors, as shown by the decrease in transverse relaxation time (T2; FIGS. 6A-B and 7). Quantitative analysis indicates a tendency towards MN-anti-miR10b build-up in the tissue after the second treatment session (FIG. 7).

Additional experiments were performed using near-infrared optical imaging to study the whole-body distribution of MN-anti-miR10b in MDA-MB-231(luc) tumor-bearing mice. The MN-RGD-anti-miR-10b used in these experiments was generated using a 23-nm magnetic nanoparticle precursor as described in Example 1. The resulting therapeutic magnetic nanoparticle, hereafter referred to as "23-nm MN-RGD-miR-10b", was injected intravenously into the MDA-MB-231(luc) tumor-bearing mouse model. Following injection, the tissue localization/bioavailability of 23-nm MN-RGD-anti-miR-10b was assessed in the mice using in vivo near-infrared optimal imaging. These experiments were performed using the methods described below.

In Vivo Optical Imaging

In vivo fluorescence optical imaging was performed immediately after each in vivo MR imaging session. Anesthetized animals were placed supine into a whole-body imaging system (IVIS Spectrum, Caliper Life Sciences) equipped with 10 narrow band excitation filters (30 nm bandwidth) and 18 narrow band emission filters (20 nm bandwidth) that assist in significantly reducing autofluorescence through spectral scanning of filters and the use of spectral unmixing algorithms (Caliper Life Sciences). The abdominal region of the animal was shielded in order to avoid interfering signal from internal organs. Imaging was performed using 675-nm excitation and 720-nm emission filters. The epifluorescent images and the grayscale photographs were acquired and superimposed.

Figure 8A:
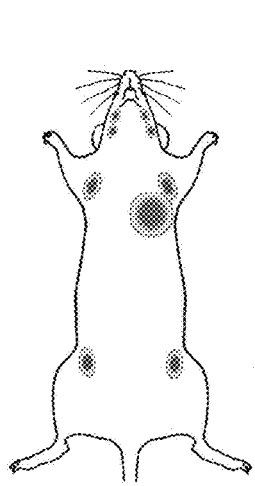
FIGS. 8A, 8B, and 8C are a series of a schematic showing the position of the primary tumor and several lymph nodes in the orthotopic MDA-MB-231-luc-D3H2LN mouse model (8A), and two near-infrared optical images showing the MN-anti-miR10b accumulation in orthotopic MDA-MB-231-luc-D3H2LN tumors before (8B) and 24-hours after (8C) MN-anti-miR10b administration.
Figures 8B, 8C:
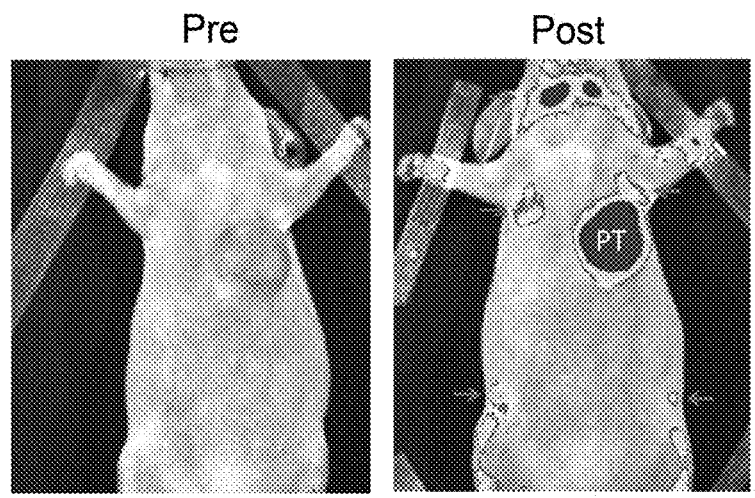

The resulting data show that 23-nm MN-RGD-anti-miR-10b was taken up by the primary tumor and lymph nodes (visible in the superficial axial, inguinal, and cervical lymph nodes) (FIGS. 8A-C). These data indicate that 23-nm MN-RGD-anti-miR-10b represents a suitable approach for delivery of an anti-miR-10b nucleic acid to both a primary tumor and lymph nodes (e.g., tumor cells present in the primary tumor and lymph nodes).

The accumulation of 23-nm MN-RGD-anti-miR-10b in the primary tumor and lymph nodes was also confirmed by ex vivo imaging. Ex vivo optical imaging was performed as described below.

Ex Vivo Optical Imaging

Ex vivo fluorescent images were acquired by placing the excised tissues in the imaging system immediately after the animals were sacrificed. The average radiance from each fluorescence reading was used to estimate nanodrug uptake. The images were reconstructed using Living Image software version 4.0 (Caliper Life Sciences).

The resulting ex vivo imaging data show that 23-nm MN-RGD-anti-miR-10b accumulated in the primary tumor and brachial lymph nodes, an inguinal lymph node, and a cervical lymph node in these tumor-bearing mice (FIGS. 9A-E). Quantitative analysis also indicates a significantly high uptake of the therapeutic magnetic nanoparticles by the primary tumor and lymph nodes relative to muscle tissue (FIG. 10).

Additional experiments were performed to determine the cellular distribution of 23-nm MN-RGD-anti-miR-10b in tumor sections from these mice. In these experiments, tumor sections from the tumor-bearing mice treated with 23-nm MN-RGD-anti-miR-10b were visualized using near-infrared fluorescence imaging (for Cy5.5). The resulting data show an extensive uptake of 23-nm MN-RGD-anti-miR-10b by the primary tumor present in these mice.

Experiments were also performed to determine whether a non-therapeutic magnetic nanoparticle (MN-RGD-scrambled nucleic acid) would be taken up by metastatic tumor cells present in the lymph node of these tumor-bearing mice. The MN-RGD-scrambled nucleic acid used in these experiments was generated by replacing the anti-miR-10b nucleic acid present in 20-nm MN-RGD-anti-miR-10b (derived from a 20-nm precursor) with a scrambled oligonucleotide. In these experiments, lymph node sections were harvested from mice injected with MN-RGD-scrambled (MN-RGD-LNA(SCR)) and the distribution/localization of the MN-RGD-LNA(SCR) was assessed using staining for Cy5.5. Additional co-staining was performed for CD68 (macrophages). These experiments were performed as described below.

Histology and Fluorescence Microscopy of Tissue Sections

To detect the metastatic lesions and/or the accumulation of the therapeutic magnetic nanoparticles in a tissue (e.g., a primary tumor, lymph nodes, or lungs), the excised tissue was embedded in Tissue-Tek OCT compound (Sakura Finetek) and snap frozen in liquid nitrogen. The frozen primary tumor and lymph nodes were cut into 7-µm sections. The lungs were cut into 30-µm sections. The sections were fixed in 2% paraformaldehyde, washed, and counterstained with Vectashield mounting medium containing 4',6-diamidino-2-phenylindole (DAPI; Vector Laboratories), and analyzed by fluorescence microscopy using a Nikon Eclipse 50i fluorescence microscope equipped with the necessary filter sets. Images were acquired using a charge-coupled device camera with near-IR sensitivity (SPOT 7.4 Slider RTKE; Diagnostic Instruments). The images were analyzed using SPOT 4.0 Advance version software (Diagnostic Instruments). The observed Cy5.5 signal within tumor sections was the result of accumulation of the intravenously-injected magnetic particles.

For macrophage staining, frozen lymph node sections were incubated with a rat anti-mouse CD68 (FA-11) antibody (Serotec) followed by a rhodamine-labeled goat secondary antibody (Abcam, Cambridge). Consecutive tissue sections were stained with hematoxylin and eosin (H&E), and analyzed by light microscopy to determine metastatic burden or to compare fluorescent images with H&E-defined tissue architecture.

The resulting data show extensive uptake of MN-antimiR10b by the primary tumor cells and that MN-RGD-LNA(SCR) is taken up by both resident macrophages in the lymph node and metastatic tumor cells located in the lymph node (metastatic tumor cells located in the paracortex outside of the lymphocyte-rich germinal centers). The data also show that in the absence of metastatic tumor cells, the therapeutic nanoparticles distributed principally to macrophages. These data indicate that the therapeutic nanoparticles described herein can target therapeutic nucleic acids to lymph nodes and can further target therapeutic nucleic acids to metastatic tumor cells present in lymph nodes.

Example 4. Therapeutic Nanoparticles Reduce Tumor Cell Metastasis In Vivo

Additional experiments were performed to determine whether administration of MN-RGD-anti-miR-10b or MN-RGD-scrambled nucleic acid (control), starting prior to the beginning of tumor cell metastasis, would reduce tumor cell metastasis in the nude mouse model of human breast cancer (i.e., the orthotopic implantation of MDA-MB-231(luc) cells into nude mice). In vivo bioluminescence imaging was used to visualize and quantify the metastatic burden from the luciferase-transformed MDA-MB-231-luc-D3H2L2 cell line. These experiments were performed as described below.

Prevention of Metastasis

Six week-old nu/nu (n=12) were injected in the upper right mammary fat pad with $2 \times 10^6$ MDA-MB-231-luc-D3H2LN cells (Caliper). The animals were used in experiments 14-days after tumor implantation.

In Vivo Optical Bioluminescence Imaging

Mice were injected in the lower left abdominal quadrant with D-Luciferin potassium salt firefly in DPBS (150 mg Luciferin/kg body weight, 200 µl of 15 mg/mL; Caliper Life Sciences) ten minutes before image acquisition. The primary tumor was shielded to prevent signal leakage into the right brachial lymph node. Identical imaging settings (time, 30-60 seconds; F-stop, 2; binning, medium) and same-size regions of interest (ROIs) were used to obtain total radiance flux of the metastatic signals from right brachial lymph nodes. The total radiance (photons/second) from the bioluminescent readings was used for signal quantification.

The resulting data show that by the end of the treatment course, the signal in experimental animals treated with MN-anti-miR10b was at pre-metastatic levels, indicating a prevention of tumor cell metastasis from primary tumor to lymph nodes (FIGS. 11A and B). In contrast, the data show a visible dissemination of tumor cells to the lymph nodes of control animals treated with MN-scr-miR. This observed therapeutic effect was highly reproducible (see FIG. 12). The therapeutic magnetic nanoparticles in this experiment had a diameter of between 20-25 nm.

Example 5. Therapeutic Nanoparticles Arrest Metastasis

Additional experiments were performed to determine whether the therapeutic magnetic nanoparticles could arrest metastatic disease once it had spread beyond the primary tumor and into the lymph nodes. In these experiments, treatment with MN-anti-miR10b was initiated four weeks after tumor cell implantation, subsequent to the formation of lymph node metastases. The methods used to perform these experiments are described above with the modifications indicated below.

Arrest of Metastasis

Six week-old NIH III nude mice (n=6) were injected in the lower left mammary fat pad with $2 \times 10^6$ MDA-MB-231-luc-D3H2LN cells (Caliper). The animals were used in experiments 28-days after tumor implantation. Treatment with MN-anti-miR10b or MN-scr-miR involved systematic administration through the tail vein at a dose of 10 mg Fe/kg once a week, over four weeks.

In Vivo Optical Bioluminecense Imaging

For the study on metastatic arrest, the lower abdominal primary tumor in the mammary fat was shielded and the total bioluminescence flux reading (photons/second) was taken from the right brachial lymph node with a fixed ROI (F-stop, 8; binning large).

Fluorescence Microscopy

For luciferase staining, frozen lung sections were incubated with a rabbit firefly luciferase antibody (Abcam, Cambridge, Mass.) followed by a DyLight® 488-labeled goat polyclonal secondary antibody to Rabbit IgG (Abcam, Cambridge, Mass.).

Western Blot

Frozen tumor sections were thawed and homogenized in tissue protein extraction lysis buffer (Tissue-PE LB from G-Biosciences, St Louis, Mo., USA) along with 1 mM phenylmethylsulfonyl fluoride (PMSF) and proteinase inhibitor cocktails (Sigma, St Louis, Mo., USA). Protein content was determined with the Bio-Rad protein assay kit (Bio-Rad, Hercules, Calif., USA). Lysates (50 mg) were separated by electrophoresis through 4-20% sodium dodecyl sulfate polyacrylamide gel electrophoresis and transferred to nitrocellulose membranes (Bio-Rad). Membranes were blocked in 5% nonfat milk in Tris-buffered saline/Tween 20 for 1 hour at room temperature.

After blocking, the membrane was incubated overnight at 41° C. in 1% milk/TBS containing HOXD10 (H-80) rabbit polyclonal antibody (1:200, Santa Cruz Biotechnology, Santa Cruz, Calif., USA) and mouse monoclonal b-actin (1 mg/ml; Applied Biosystems, Carlsbad, Calif., USA). The membrane was then washed three times with 0.05% Tween TBS (TBST) for 5 minutes each and incubated with horseradish peroxidase-conjugated goat anti-rabbit or anti-mouse antibodies (Invitrogen, Camarillo, Calif., USA) (1:2000 dilution) for 60 minutes at room temperature, followed by washing three times with TBST and one time with TBS for 5 minutes each. Membranes were finally developed using ECL plus western blotting detection reagents kit (GE Healthcare), according to the manufacturer's specifications.

Figure 18:
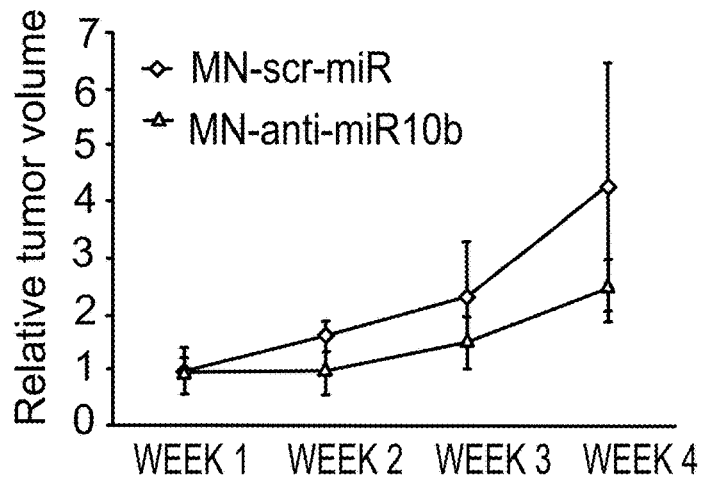
FIG. 18 is a graph showing the effect on relative MDA-MB-231-D3H2LN in mice treated with the MN-anti-miR10b compared to the radiance of brachial lymph nodes from tumor-bearing mice treated with MN-scr-miR at different time points subsequent to lymph node metastasis. There was no significant difference between experimental and control animals, incicating a lack of miR-10b influence on primary tumor growth (n=6).
Figure 19:
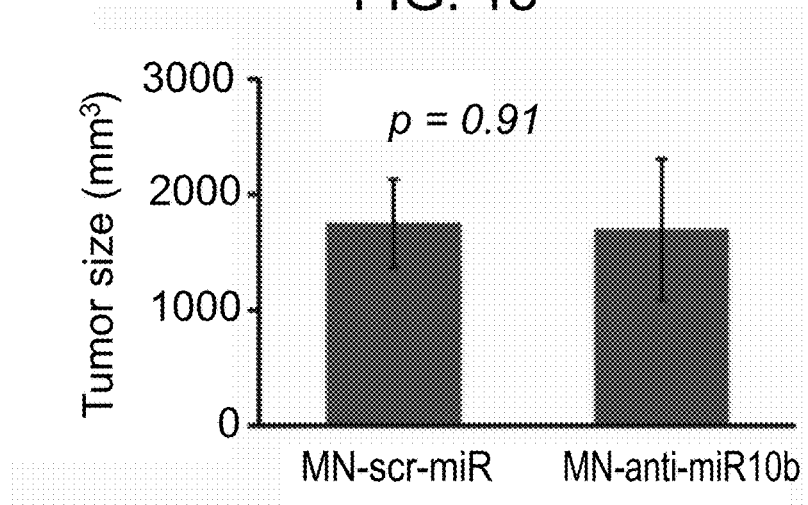
FIG. 19 is a graph showing the tumor size of MDA-MB-231-D3H2LN tumors excised from mice treated with MN-anti-miR10b compared to MDA-MB-231-D3H2LN tumors excised form mice treated MN-scr-miR.
Figure 20:
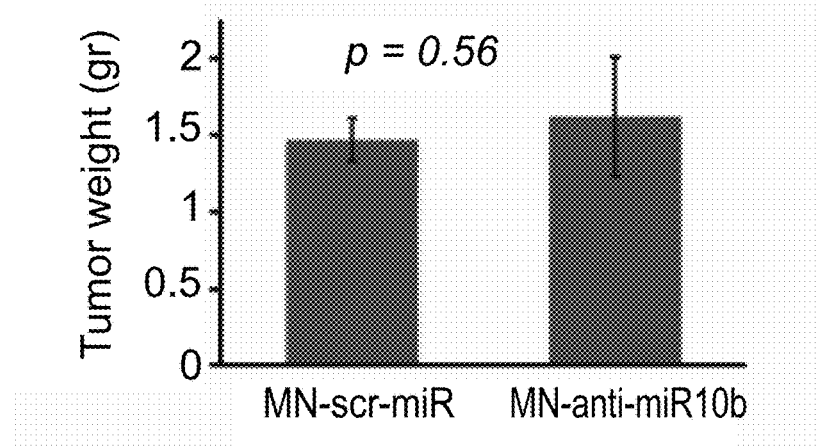
FIG. 20 is a graph showing the tumor weight of MDA-MB-231-D3H2LN tumors excised from mice treated with MN-anti-miR10b compared to MDA-MB-231-D3H2LN tumors excised form mice treated MN-scr-miR.
Figure 21:
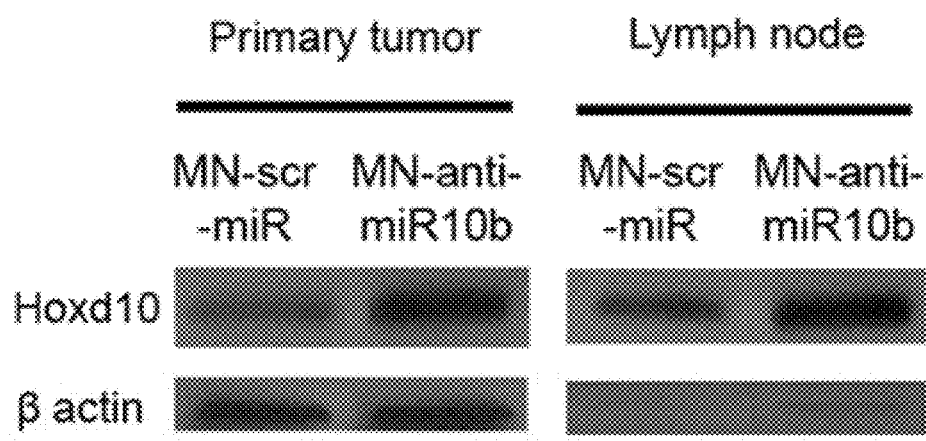
FIG. 21 is a set of Western blots showing an increase in HOXD10 expression levels in MDA-MB-231-D3H2LN tumors and the lymph nodes with metastatic burden after systematic MN-anti-miR10b administration.

The resulting data show that there was a complete arrest of metastasis in the experimental animals treated with MN-anti-miR10b (see FIGS. 13A-D and 14). In contrast, mice treated with control MN-scr-miR had a 20-fold increase in lymph node metastatic burden (FIG. 14), without a concomitant effect on primary tumor growth (see FIGS. 18 and 19). This effect was accompanied by induction of the known miR-10b target HOXD106 (see FIG. 21) at both sites indicating that the function of miR-10b in tumor cell migration is conserved between the primary and lymph node metastatic tumor cells.

Figures 15A, 15B:
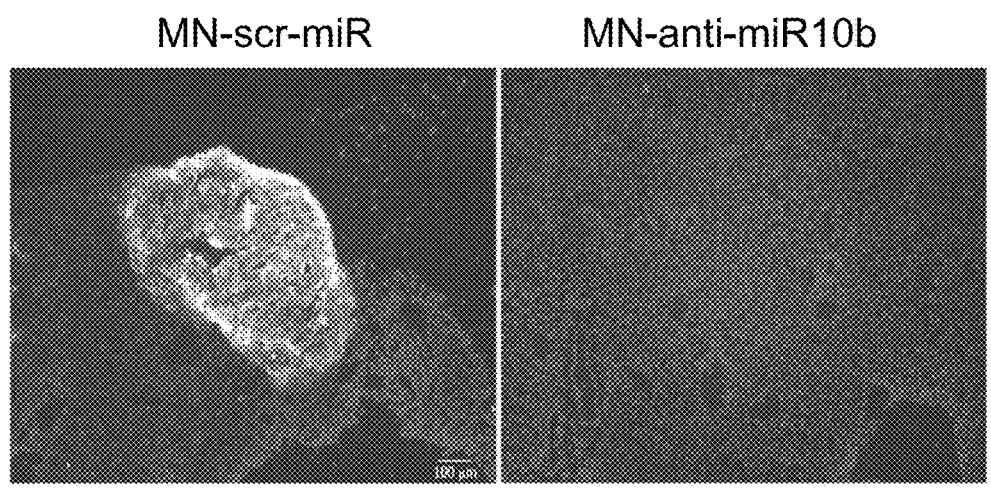
FIGS. 15A and 15B are two immunofluorence images of lung tissue in the tumor-bearing MDA-MB-231-luc-D3H2LN mouse model treated with MN-anti-miR10b (15B) or MN-scr-miR (15A) beginning subsequent to lymph node metastasis. Light shading indicates the presence of lung metastases in the MDA-MB-231-luc-DH2LN mouse model.

The therapeutic effect of MN-anti-miR-10b also manifested as a decrease in distant metastasis. In the lungs of mice treated with MN-scr-miR, following the formation of metastasis in the lymph node, there were distinct infiltrates of tumor cells; however, no tumor cells were detected in the lungs of mice treated with MN-anti-miR10b, following the formation of metastasis in the lymph node (FIGS. 15A and 15B). These data indicate that the magnetic particles described herein can arrest the metastatic process and prevent further tumor cell colonization of distant organs (prevent or reduce further metastasis from a lymph node to a secondary tissue).

Example 6. Therapeutic Nanoparticles Arrest Metastasis in the Absence of a Primary Tumor Additional experiments were performed to determine whether the therapeutic magnetic nanoparticles could arrest lymph node metastasis in the absence of a primary tumor. In these experiments, the primary tumors were surgically removed after establishment of lymph node metastasis and prior to the initiation of therapy. The methods used to perform these experiments are described above with the modifications indicated below.

Arrest of Metastasis in Mice with Surgically Removed Primary Tumor

Six-week-old nu/nu mice were injected in the lower left mammary fat pad with 2×106 MDA-MB-231-luc-D3H2LN cells (Caliper). Tumors were surgically removed 28 days after tumor implantation. Treatment with MN-anti-miR10b and MN-scr-miR involved systematic administration through the tail vein at a dose of 10 mg Fe/kg once a week over 4 weeks.

In Vivo Optical Bioluminecense Imaging

For the study on metastatic arrest, the lower abdominal primary tumor in the mammary fat was shielded and the total bioluminescence flux reading (photons/second) was taken from the right brachial lymph node with a fixed ROI (F-stop, 8; binning large).

Figure 22:
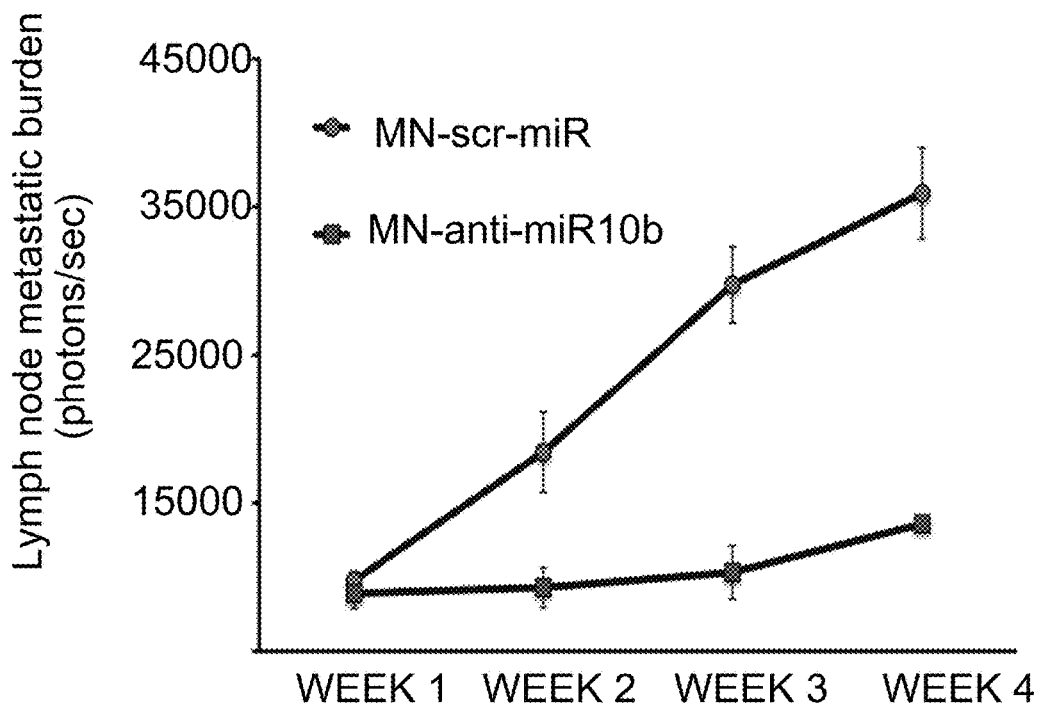
FIG. 22 is a graph showing the lymph node metastatic burden following treatment with MN-anti-miR10b in the absence of a primary tumor. The data shown are the mean±standard error (n=6).

The resulting data show there was an increase in bioluminescence signal from the brachial lymph nodes, consistent with metastatic expansion. (FIG. 22) By contrast, bioluminescence in the experimental animals remained at pre-treatment levels, indicating that MN-anti-miR10b could arrest the expansion of pre-established metastases. (FIG. 22)

Overall, the data described herein indicate that the therapeutic nanoparticles described herein can decrease tumor cell metastasis from a primary tumor in a mammal (e.g., decrease tumor cell metastasis from a primary tumor to a lymph node) and can further prevent or decrease tumor cell metastasis from the lymph node to a secondary tissue in a mammal. These data show that dextran-coated nanoparticles (e.g., 15-25 nm in diameter) are lymphotropic, with up to 9% of the injected dose accumulating in lymph nodes. The increased uptake by lymph nodes is particularly important when attempting to decrease or arrest metastatic process after the primary tumor cells have disseminated to lymph nodes in a mammal. The data further show that a significant fraction of the administered therapeutic nanoparticles are taken up by macrophages, as well as metastatic tumor cells, present in the lymph nodes.

Finally, these data suggest that the therapeutic nanoparticles provided herein can be used to target therapeutic nucleic acids to metastatic tumor cells present in the lymph node, wherein the therapeutic nucleic acids result in a decrease or the stabilization of metastatic tumor size or result in a decrease in metastatic tumor growth.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A therapeutic nanoparticle, wherein said therapeutic nanoparticle:
   comprises a polymer coating, and
   a nucleic acid comprising at least 10 contiguous nucleotides within the sequence of CACAAATTCGGTTCTACAGGGTA (SEQ ID NO: 18) that is covalently linked to a nanoparticle.

2. The therapeutic nanoparticle of claim 1, wherein the nucleic acid comprises SEQ ID NO: 18.

3. The therapeutic nanoparticle of claim 1, wherein the nucleic acid comprises at least one modified nucleotide.

4. The therapeutic nanoparticle of claim 3, wherein the at least one modified nucleotide is a locked nucleotide.

5. The therapeutic nanoparticle of claim 1, wherein the nanoparticle further comprises a covalently-linked fluorophore.

6. The therapeutic nanoparticle of claim 5, wherein the fluorophore absorbs near-infrared light.

7. The therapeutic nanoparticle of claim 5, wherein the fluorophore is covalently-linked to the nanoparticle through a chemical moiety comprising a secondary amine.

8. The therapeutic nanoparticle of claim 1, wherein the polymer coating comprises dextran.

9. The therapeutic nanoparticle of claim 1, wherein the nucleic acid is a small interfering RNA (siRNA) molecule.

10. The therapeutic nanoparticle of claim 1, wherein the nucleic acid is covalently-linked to the nanoparticle through a chemical moiety comprising a disulfide bond or a thioether bond.

11. The therapeutic nanoparticle of claim 1, wherein the nanoparticle is magnetic.

12. A pharmaceutical composition comprising the therapeutic nanoparticle of claim 1 and a pharmaceutically acceptable carrier.

13. A method for treating a metastatic cancer in a subject, the method comprising:
   administering to the subject in need thereof a therapeutic nanoparticle comprising a polymer coating and a nucleic acid comprising at least 10 contiguous nucleotides within the sequence of CACAAATTCGGTTC-TACAGGGTA (SEQ ID NO: 18) that is covalently or non-covalently linked to a nanoparticle,
   wherein the therapeutic nanoparticle is administered in an amount sufficient to treat the metastatic cancer in the subject.

14. The method of claim 13, wherein the therapeutic nanoparticle is administered to the subject by intravenous administration, subcutaneous, intraarterial, intramuscular, or intraperitoneal administration.

15. The method of claim 13, wherein the metastatic cancer is localized in breast, lymph nodes, lung, bone, brain, liver, ovary, peritoneum, muscle tissue, pancreas, prostate, esophagus, colon, rectum, stomach, nasopharyngeal or skin.

16. The method of claim 13, wherein the nucleic acid comprises SEQ ID NO: 18.

17. The method of claim 13, wherein the nucleic acid comprises at least one modified nucleotide.

18. The method of claim 17, wherein the at least one modified nucleotide is a locked nucleotide.

19. The method of claim 13, wherein the therapeutic nanoparticle further comprises a covalently-linked fluorophore.

20. The method of claim 19, wherein the fluorophore absorbs near-infrared light.

21. The method of claim 19, wherein the fluorophore is covalently-linked to the therapeutic nanoparticle through a chemical moiety comprising a secondary amine.

22. The method of claim 13, wherein the polymer coating comprises dextran.

23. The method of claim 13, wherein the nucleic acid is covalently linked to the therapeutic nanoparticle through a chemical moiety comprising a disulfide bond or a thioether bond.

24. The method of claim 13, further comprising administering one or more additional chemotherapeutic agents, wherein the one or more additional chemotherapeutic agents is administered prior, concurrently, or after administration of the therapeutic nanoparticle.

25. The method of claim 24, wherein the one or more additional chemotherapeutic agents are selected from the group consisting of cyclophosphamide, mechlorethamine, chlorambucil, melphalan, daunorubicin, doxorubicin, epirubicin, idarubicin, mitoxantrone, valrubicin, paclitaxel, docetaxel, etoposide, teniposide, tafluposide, azacitidine, azathioprine, capecitabine, cytarabine, doxifluridine, fluorouracil, gemcitabine, mercaptopurine, methotrexate, tioguanine, bleomycin, carboplatin, cisplatin, oxaliplatin, all-trans retinoic acid, vinblastine, vincristine, vindesine, vinorelbine, and bevacizumab.

26. The method of claim 13, further comprising administering a radiotherapy treatment.

27. The method of claim 13, further comprising administering molecularly targeted therapy.

28. The method of claim 27, wherein the molecularly targeted therapy is Herceptin.

* * * * *

SEQUENCE LISTING

```
<160> NUMBER OF SEQ ID NOS: 20

<210> SEQ ID NO 1
<211> LENGTH: 23
<212> TYPE: DNA
<213> ORGANISM: Artificial Sequence
<220> FEATURE:
<223> OTHER INFORMATION: Synthetic nucleotide

<400> SEQUENCE: 1
atgggacatc ttggcttaaa cac                                             23
```

```
<210> SEQ ID NO 2
<211> LENGTH: 22
<212> TYPE: DNA
<213> ORGANISM: Artificial Sequence
<220> FEATURE:
<223> OTHER INFORMATION: Synthetic nucleotide

<400> SEQUENCE: 2
tgtctaagct aagatcccct ta                                              22

<210> SEQ ID NO 3
<211> LENGTH: 23
<212> TYPE: RNA
<213> ORGANISM: Homo sapiens

<400> SEQUENCE: 3
uacccuguag aaccgaauuu gug                                             23

<210> SEQ ID NO 4
<211> LENGTH: 22
<212> TYPE: RNA
<213> ORGANISM: Homo sapiens

<400> SEQUENCE: 4
acagauucga uucuagggga au                                              22

<210> SEQ ID NO 5
<211> LENGTH: 22
<212> TYPE: RNA
<213> ORGANISM: Homo sapiens

<400> SEQUENCE: 5
ucccugagac ccuaacuugu ga                                              22

<210> SEQ ID NO 6
<211> LENGTH: 22
<212> TYPE: RNA
<213> ORGANISM: Homo sapiens

<400> SEQUENCE: 6
ucccugagac ccuaacuugu ga                                              22

<210> SEQ ID NO 7
<211> LENGTH: 22
<212> TYPE: RNA
<213> ORGANISM: Homo sapiens

<400> SEQUENCE: 7
ucccugagac ccuaacuugu ga                                              22

<210> SEQ ID NO 8
<211> LENGTH: 22
<212> TYPE: RNA
<213> ORGANISM: Homo sapiens

<400> SEQUENCE: 8
ucacaaguca ggcucuuggg ac                                              22

<210> SEQ ID NO 9
<211> LENGTH: 22
<212> TYPE: RNA
<213> ORGANISM: Homo sapiens
```

```
<400> SEQUENCE: 9
cauugcacuu gucucggucu ga                                              22

<210> SEQ ID NO 10
<211> LENGTH: 21
<212> TYPE: RNA
<213> ORGANISM: Homo sapiens

<400> SEQUENCE: 10
aggcggagac uugggcaauu g                                               21

<210> SEQ ID NO 11
<211> LENGTH: 12
<212> TYPE: PRT
<213> ORGANISM: Artificial Sequence
<220> FEATURE:
<223> OTHER INFORMATION: Targeting peptide

<400> SEQUENCE: 11

Asn Tyr Leu His Asn His Pro Tyr Gly Thr Val Gly
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Targeting peptide

<400> SEQUENCE: 12

Ser Asn Pro Phe Ser Lys Pro Tyr Gly Leu Thr Val
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Targeting peptide

<400> SEQUENCE: 13

Gly Leu His Glu Ser Thr Phe Thr Gln Arg Arg Leu
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Targeting peptide

<400> SEQUENCE: 14

Tyr Pro His Tyr Ser Leu Pro Gly Ser Ser Thr Leu
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Targeting peptide

<400> SEQUENCE: 15

Ser Ser Leu Glu Pro Trp His Arg Thr Thr Ser Arg
1               5                   10
```

```
<210> SEQ ID NO 16
<211> LENGTH: 12
<212> TYPE: PRT
<213> ORGANISM: Artificial Sequence
<220> FEATURE:
<223> OTHER INFORMATION: Targeting peptide

<400> SEQUENCE: 16

Leu Pro Leu Ala Leu Pro Arg His Asn Ala Ser Val
1               5                   10

<210> SEQ ID NO 17
<211> LENGTH: 22
<212> TYPE: DNA
<213> ORGANISM: Artificial Sequence
<220> FEATURE:
<223> OTHER INFORMATION: Synthetic nucleotide

<400> SEQUENCE: 17
gtgtaacacg tctatacgcc ca                                          22

<210> SEQ ID NO 18
<211> LENGTH: 23
<212> TYPE: DNA
<213> ORGANISM: Artificial Sequence
<220> FEATURE:
<223> OTHER INFORMATION: Synthetic nucleotide

<400> SEQUENCE: 18
cacaaattcg gttctacagg gta                                         23

<210> SEQ ID NO 19
<211> LENGTH: 9
<212> TYPE: PRT
<213> ORGANISM: Artificial Sequence
<220> FEATURE:
<223> OTHER INFORMATION: Targeting peptide

<400> SEQUENCE: 19

Ala Arg Arg Arg Arg Arg Arg Arg Cys
1               5

<210> SEQ ID NO 20
<211> LENGTH: 110
<212> TYPE: RNA
<213> ORGANISM: Homo sapiens

<400> SEQUENCE: 20
ccagagguug uaacguuguc uauauauacc cuguagaacc gaauuugugu gguauccgua    60
uagucacaga uucgauucua ggggaauaua uggucgaugc aaaaacuuca              110
```